US010190960B2

(12) United States Patent
Sharpe et al.

(10) Patent No.: US 10,190,960 B2
(45) Date of Patent: Jan. 29, 2019

(54) MICRO-LENS SYSTEMS FOR PARTICLE PROCESSING SYSTEMS

(71) Applicant: CYTONOME/ST, LLC, Boston, MA (US)

(72) Inventors: Johnathan Charles Sharpe, Hamilton (NZ); Donald Francis Perrault, Jr., Brighton, MA (US)

(73) Assignee: CYTONOME/ST, LLC, Bedford, MA (US)

( * ) Notice: Subject to any disclaimer, the term of this patent is extended or adjusted under 35 U.S.C. 154(b) by 502 days.

(21) Appl. No.: 14/208,283

(22) Filed: Mar. 13, 2014

(65) Prior Publication Data
US 2014/0339445 A1 Nov. 20, 2014

Related U.S. Application Data

(60) Provisional application No. 61/784,323, filed on Mar. 14, 2013.

(51) Int. Cl.
*G01N 15/14* (2006.01)
*G01N 21/64* (2006.01)
*G01N 15/10* (2006.01)
*G02B 3/00* (2006.01)
*G02B 5/09* (2006.01)

(52) U.S. Cl.
CPC ..... *G01N 15/1434* (2013.01); *G01N 15/1459* (2013.01); *G01N 15/1484* (2013.01); *G01N 21/64* (2013.01); *G01N 2015/1006* (2013.01); *G01N 2015/1081* (2013.01);

(Continued)

(58) Field of Classification Search
CPC .......... G01N 15/1459; G01N 15/1434; G01N 15/1484; G01N 21/64; G01N 2015/1081; G01N 2015/1006; G01N 2015/149; G02B 3/0037; G02B 3/0087; G02B 5/09
See application file for complete search history.

(56) References Cited

U.S. PATENT DOCUMENTS 6,248,590 B1 6/2001 Malachowski
6,316,781 B1 11/2001 Nagle et al.
(Continued)

FOREIGN PATENT DOCUMENTS

WO 2004/088283 A2 10/2004
WO 2009/073649 A1 6/2009
WO 2010/045949 A2 4/2010

OTHER PUBLICATIONS

Extended European Search Report for Application No. EP 14159719, dated Apr. 5, 2015.

(Continued)

*Primary Examiner* — John Lee
(74) *Attorney, Agent, or Firm* — McCarter & English, LLP; David R. Burns

(57) ABSTRACT

The present disclosure provides improved optical systems for particle processing (e.g., cytometry including microfluidic based sorters, drop sorters, and/or cell purification) systems and methods. More particularly, the present disclosure provides advantageous micro-lens array optical detection assemblies for particle (e.g., cells, microscopic particles, etc.) processing systems and methods (e.g., for analyzing, sorting, processing, purifying, measuring, isolating, detecting, monitoring and/or enriching particles.

26 Claims, 15 Drawing Sheets

(52) U.S. Cl.
CPC ...... *G01N 2015/149* (2013.01); *G02B 3/0037* (2013.01); *G02B 3/0087* (2013.01); *G02B 5/09* (2013.01)

(56) References Cited

U.S. PATENT DOCUMENTS

| | | | |
|---|---|---|---|
| 6,700,130 B2 | 3/2004 | Fritz | |
| 6,808,075 B2 | 10/2004 | Bohm et al. | |
| 7,253,958 B2* | 8/2007 | Aizenberg | G02B 1/041 359/619 |
| 7,309,409 B2* | 12/2007 | Amirkhanian | G01N 27/44782 204/603 |
| 7,400,380 B2* | 7/2008 | Hahn | G03F 7/70291 355/53 |
| 7,492,522 B2 | 2/2009 | Gilbert et al. | |
| 7,557,337 B2* | 7/2009 | Jiang | H01L 27/14627 250/216 |
| 7,569,788 B2 | 8/2009 | Deshpande et al. | |
| 7,671,987 B2 | 3/2010 | Padmanabhan et al. | |
| 8,123,044 B2 | 2/2012 | Johnson et al. | |
| 8,274,040 B2* | 9/2012 | Zhong | G01N 21/648 250/239 |
| 8,277,764 B2 | 10/2012 | Gilbert et al. | |
| 8,471,230 B2* | 6/2013 | Zhong | G01N 21/648 250/221 |
| 8,529,161 B2 | 9/2013 | Gilbert et al. | |
| 9,410,891 B2* | 8/2016 | Fehr | B01L 3/502707 |
| 2002/0123073 A1* | 9/2002 | Amirkhanian | G01N 27/44782 435/7.1 |
| 2003/0017079 A1* | 1/2003 | Hahn | B01L 3/502715 422/82.09 |
| 2005/0112541 A1* | 5/2005 | Durack | C12N 5/0612 435/2 |
| 2009/0116005 A1 | 5/2009 | Furuki et al. | |
| 2010/0065726 A1* | 3/2010 | Zhong | G01N 21/648 250/227.24 |
| 2010/0096560 A1 | 4/2010 | Imanishi et al. | |
| 2011/0165652 A1* | 7/2011 | Hardin | C07H 19/10 435/194 |
| 2011/0196637 A1 | 8/2011 | Sharpe et al. | |
| 2011/0222051 A1 | 9/2011 | Heng | |
| 2012/0277902 A1 | 11/2012 | Sharpe et al. | |
| 2013/0334407 A1 | 12/2013 | Perrault, Jr. et al. | |
| 2014/0085898 A1 | 3/2014 | Perrault, Jr. | |
| 2014/0339445 A1* | 11/2014 | Sharpe | G01N 15/1459 250/574 |

OTHER PUBLICATIONS

Roulet et al., "Fabrication of Multilayer Systems Combining Microfluidic and Microoptical Elements for Fluorescence Detection," J. Microelectromechanical Sys., 10(4):482-491 (2001).

Schonbrun et al., "A Microfluidic Fluorescence Measurement System Using an Astigmatic Diffractive Microlens Array," Optics Express, 19(2):1385-1394 (2011).

European Search Report for Application No. 14159719.5, dated Feb. 1, 2018. 7 pages.

Roulet et al., Fabrication of Multilayer Systems Combining Microfluidic and Microoptical Elements for Fluorescence Detection. J Microelectromechanical Sys. Dec. 2001;10(4):482-491.

Schonbrun et al., A microfluidic fluorescence measurement system using an astigmatic diffractive microlens array. Opt Express. Jan. 17, 2011;19(2):1385-94.

* cited by examiner

FIG. 2
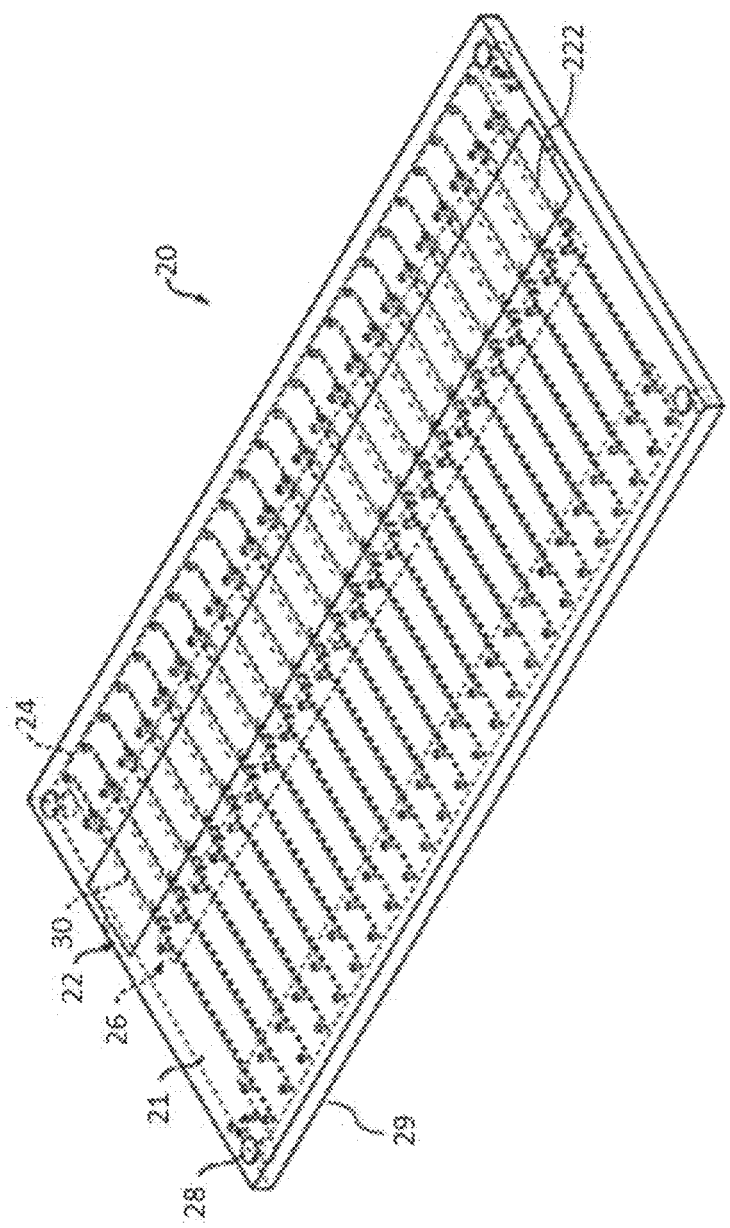
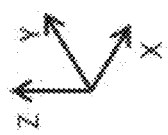

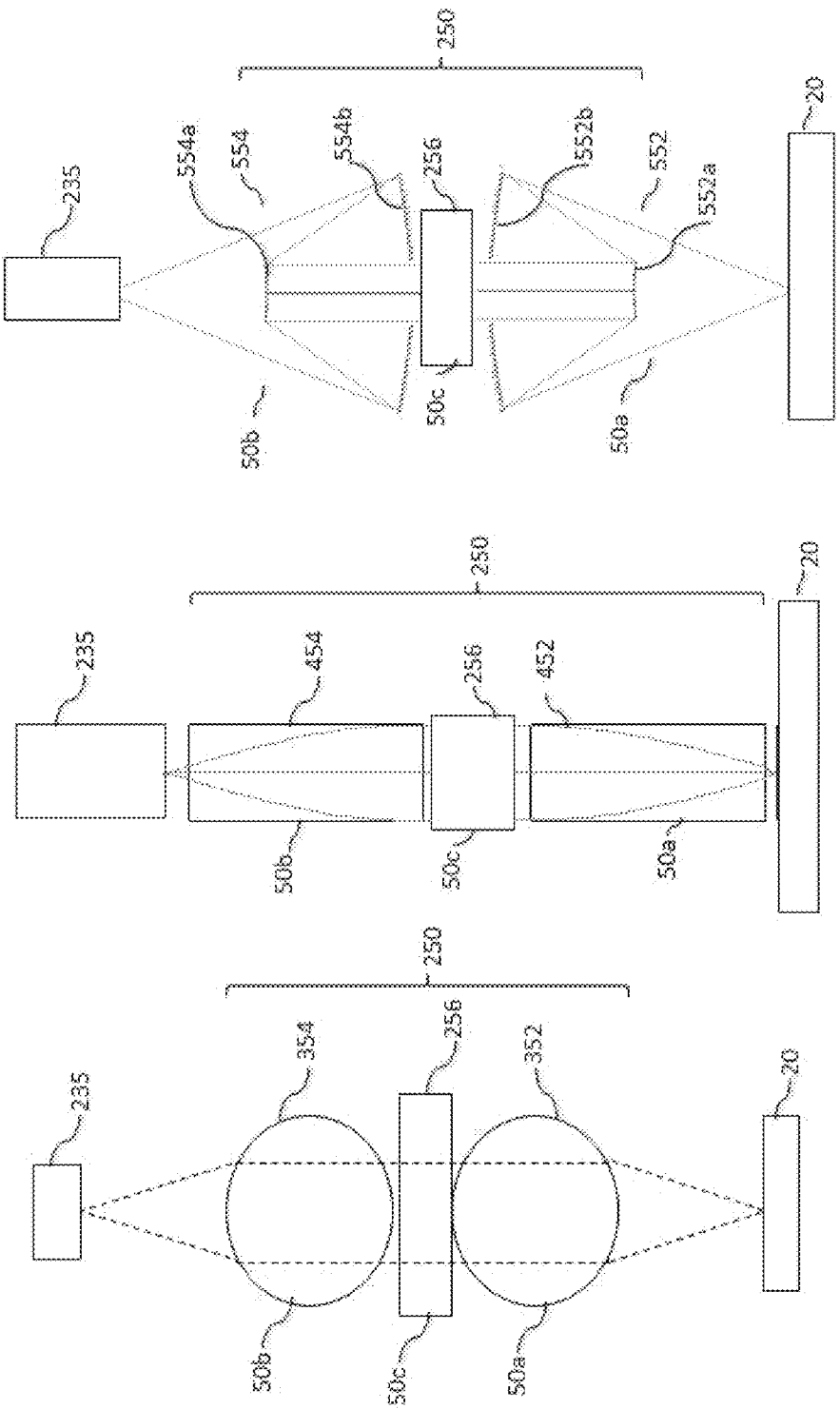

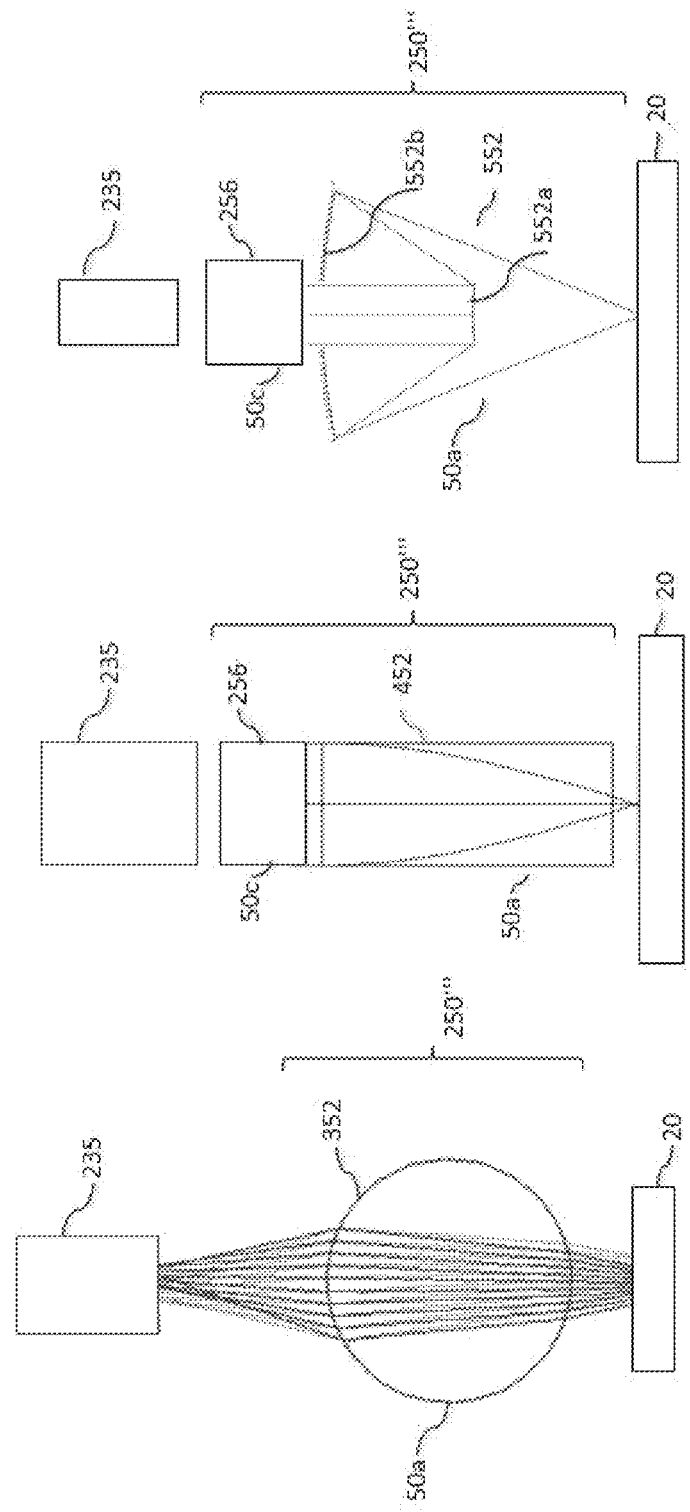

ID BO-LENS SYSTEMS FOR PARTICLE
PROCESSING SYSTEMS

RELATED APPLICATION

This application claims the benefit of priority to U.S. Provisional Application Ser. No. 61/784,323, titled "Micro-Lens Array Optical Detection for Particle Processing Systems and Related Methods of Use," filed on Mar. 14, 2013, the content of which is hereby incorporated by reference in its entirety.

TECHNICAL FIELD

The present disclosure relates to optical systems for particle processing (e.g., cytometry including microfluidic based sorters, drop formation based sorters, and/or cell purification) systems and methods and, more particularly, to micro-lens array optical assemblies for particle (e.g., cells, microscopic particles, etc.) processing systems and methods (e.g., for analyzing, sorting, processing, purifying, measuring, isolating, detecting, monitoring and/or enriching particles).

BACKGROUND

In general, particle processing (e.g., cytometry) systems (e.g., cytometers) and methods are known. For example, some approaches to particle processing or analyzing (e.g., cell purification) systems such as sorting flow cytometers and other particle processing systems have proven to be useful in life science research, industrial, diagnostics, and other medical applications.

In general, a cytometer can be described as a system that can measure large numbers of homogeneous and/or heterogeneous particle sets to achieve statistically relevant data sets that can be used to group and/or identify subpopulations that reside within a given particle population (e.g., within one or more samples). These measurements are sometimes performed optically (whether they are intrinsic or responsive to an optical stimulus), or they may be electrical in nature (or some other physical, chemical, or biological characteristic) as a stream of particles passes through a measurement or inspection zone. The particle sets may include biological entities such as cells (e.g., bacteria, viruses, organelles, yeasts, spores, genetic material, spermatozoa, egg cells, multicellular organisms, etc.), or other organisms, or other naturally occurring or synthetic/synthetically derived objects.

With the addition of sort functionality, a cytometer can also be used to isolate (e.g., physically separate) one or more particles of interest from a given sample through operator control. See, e.g., U.S. Pat. No. 6,248,590, the entire contents of which is hereby incorporated by reference in its entirety. In general, this technique can be used to classify and/or separate (e.g., purify or enrich) one or more populations as defined by the operator.

SUMMARY

According to certain aspects a particle processing system may include a particle processing region and a detection region. The detection region may include a micro-lens array optical assembly. The particle processing region, detection region and micro-lens array optical assembly are configured and adapted to process particles. The micro-lens array optical assembly may include an aspheric lens system or an aspheric micro-lens array optical assembly. The micro-lens array optical assembly may include one or more of the following features: common housing, a tilt to the lens system to avoid blocking other light paths, a finely ground bevel to the lens array and/or housing, spectrally and/or spatially selective optical elements or optical filters within the housing, isolation of optical paths, and/or optical collection fibers and/or detectors.

According to other aspects, a particle processing system may include a detection region including a micro-lens array and a particle processing region configured to be removably and optically coupled to the detection region. The particle processing region may include a microfluidic channel. The micro-lens array may include a micro-lens system associated with and in optical communication with the microfluidic channel. The micro-lens system may include a single lens, multiple lenses (refractive, diffractive, Fresnel, gradient index (GRIN), reflective mirrors, etc.) According to some embodiments, the micro-lens system may include at least two aspheric lenses.

The particle processing system may further include a microfluidic chip having a plurality of particle interrogation regions and a plurality of detector assemblies configured to receive a fluorescence signal, an extinction signal and/or a scatter signal emitted from the particle interrogation regions. A micro-lens array including a plurality of micro-lens systems may be provided. The particle processing system also include a receptacle for removably receiving the microfluidic chip, wherein the microfluidic chip has a plurality of microfluidic channels, and one or more light sources for illuminating the particle interrogation regions.

The micro-lens array may be configured to collect fluorescence (or other) signals from the plurality of particle interrogation regions. In some embodiments, the micro-lens array may have a non-zero working distance to the microfluidic chip. The micro-lens array may have a working distance to the microfluidic chip ranging from approximately 50 microns to approximately 50 mm. The working distance may include an air gap or other optically transmissive material. The micro-lens system may include free space optics. The micro-lens system may include a plurality of optical elements. A cross-section dimension of at least one of the optical elements may be approximately equal to or greater than the width of the micro-channel or the spacing between adjacent micro channels.

According to another aspect, a particle processing system may include an electromagnetic radiation source; a signal detector assembly; a microfluidic chip holder configured to removably receive a microfluidic chip having at least one particle interrogation region; and a micro-lens system configured to collect signals from the particle interrogation region. The signal detector assembly may be at least one of a fluorescence signal detector assembly, an extinction signal detector assembly, or a scatter signal detector assembly. According to certain embodiments, the signal detector assembly may include a fluorescence detector assembly and at least one of an extinction signal detector assembly and a scatter signal detector assembly. According to certain embodiments, the micro-lens system may be configured to collect fluorescence signals from the particle interrogation region. The particle processing system may also include a fiber optic array configured to receive and transmit a signal to the extinction detector assembly and/or the scatter detector assembly.

A micro-lens array having a plurality of the micro-lens systems may be provided. Each micro-lens system may have a plurality of optical elements. At least one of the optical elements may be an aspheric lens, a spherical lens, a reflective mirror array, or a gradient index lens. At least one of the optical elements may collect and collimate and/or focus a fluorescence signal, a scatter signal, and/or an extinction signal. At least one of the optical elements may have a flat region formed on a side surface. The flat region may be angled relative to the optical centerline of the optical component. At least one of the optical elements may be asymmetric with respect to the optical axis of the optical element. At least one of the optical elements may have a first surface facing the particle interrogation region, the first surface having an asymmetric cross-section. According to some embodiments, at least one of the optical elements may have a diameter less than 1.0 mm. According to certain embodiments, at least one of the optical elements may have a diameter less than 3.0 mm. According to other embodiments, at least one of the optical elements may have a diameter less than 25 mm.

According to certain aspects, each micro-lens system may collect a fluorescence signal from a single micro channel. According to certain embodiments, each micro-lens system may collimate a fluorescence signal from a single micro channel. Additionally or alternatively, each micro-lens system may focus a fluorescence signal from a single micro channel. The micro-lens system may collect fluorescence signals from a plurality of interrogation regions.

According to other aspects, each micro-lens system may collect a light scatter signal from a single micro channel. According to certain embodiments, each micro-lens system may collimate a scatter signal from a single micro channel. Additionally or alternatively, each micro-lens system may focus a scatter signal from a single micro channel. The micro-lens system may collect scatter signals from a plurality of interrogation regions.

According to other aspects, an optical axis of the micro-lens systems may be oriented at an angle from the perpendicular to a micro channel provided in the microfluidic chip. The angle from the perpendicular may be up to approximately 60 degrees, and according to some embodiments, may range from approximately 5 to approximately 60 degrees.

According to various aspects, the micro-lens system may consist of only an aspheric lens; only two aspheric lenses; only an aspheric lens and a filter; or only two aspheric lenses and a filter. According to various other aspects, the micro-lens system may consist of only a gradient index lens; only two gradient index lenses; only a gradient index lens and a filter; or only two gradient index lenses and a filter. According to even other aspects, the micro-lens system may consist of only a spherical lens; only two spherical lenses; only a spherical lens and a filter; or only two spherical lenses and a filter. According to still other aspects, the micro-lens system may consist of only a reflective mirror arrays; only two reflective mirror arrays; only a reflective mirror array and a filter; or only two reflective mirror arrays and a filter.

According to certain aspects, the micro-lens system may include one or more refractive and/or diffractive lenses. The micro-lens system may include a spectral filter or spectral dispersing element. The micro-lens system may include one or more gradient index lens. The micro-lens system may include one or more reflective mirror elements. The micro-lens system may include one or more spherical lenses. The micro-lens system may include one or more cylindrical lenses. The micro-lens system may include one or more spatial filters and/or spectral filters. The micro-lens system may include one or more multi-element lenses. The micro-lens system may include any combination of the above-noted elements.

According to yet another aspect, a micro-lens array may include a first mounting portion have a first through hole configured to accommodate a first lens for collecting and collimating a fluorescence signal and second mounting portion have a second through hole configured to accommodate a second lens for collecting and focusing the collimated fluorescence signal, and wherein the first and second mounting portions are assembled with the first and second through holes aligned with one another. At least one of the first through hole and the second through hole may be configured to accommodate a filter.

Any combination or permutation of embodiments is envisioned. Additional advantageous features, functions and applications of the disclosed systems, assemblies and methods of the present disclosure will be apparent from the description which follows, particularly when read in conjunction with the appended figures.

BRIEF DESCRIPTION OF THE DRAWINGS

Exemplary embodiments of the present disclosure are further described with reference to the appended figures. It is to be noted that the various features and combinations of features described below and illustrated in the figures can be arranged and/organized differently to result in embodiments which are still within the spirit and scope of the present disclosure. To assist those of ordinary skill in the art in making and using the disclosed systems, assemblies and methods, reference is made to the appended figures, wherein:

FIG. 2 illustrates an exemplary microfluidic chip according to the present disclosure;

FIGS. 8A, 9A and 10A schematically illustrate exemplary particle processing systems and micro-lens systems according to the present disclosure;

FIGS. 8B, 9B and 10B schematically illustrate variations of the exemplary particle processing systems and micro-lens systems of FIGS. 8A, 9A and 10A;

In the description that follows, like parts are marked throughout the specification and drawings with the same reference numerals, respectively. Drawing figures are not necessarily to scale and in certain views, parts may have been exaggerated for purposes of clarity.

DETAILED DESCRIPTION

Figure 1:
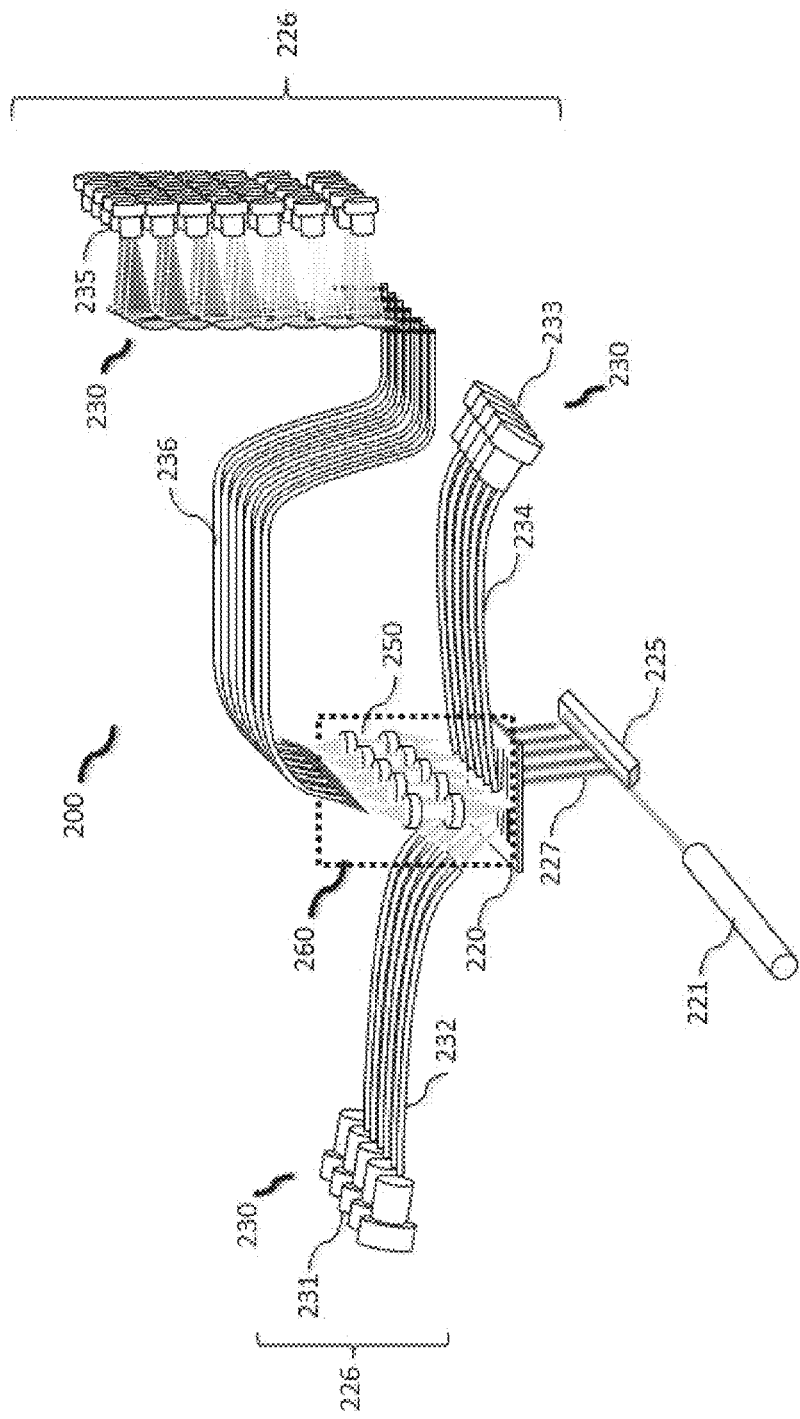
FIG. 1 schematically illustrates an exemplary particle processing system according to the present disclosure.

The present disclosure provides improved optical systems for particle processing (e.g., cytometry including microfluidic based sorters, drop formation based sorters, and/or cell purification) systems and methods. More particularly, the present disclosure advantageously provides micro-lens array optical assemblies for particle (e.g., cells, microscopic particles, etc.) processing systems and methods (e.g., for analyzing, sorting, processing, purifying, measuring, isolating, detecting, monitoring and/or enriching particles), thereby providing a significant commercial and/or operational advantage as a result.

The present disclosure provides advantageous optical systems for particle processing systems and methods. More particularly, the present disclosure provides micro-lens array optical detection assemblies for particle processing systems and methods (e.g., for analyzing, sorting, processing, purifying, measuring, isolating, detecting, monitoring and/or enriching particles).

In exemplary embodiments, a particle processing system for acquiring fluorescence signals, scatter signals (side and/or forward/backward), and/or extinction signals, etc. from a plurality of spatially separated jets and/or channels includes one or more light sources for producing a light beam that passes through the jets and/or channels to be monitored, one or more micro-lens systems for capturing the light from the light source(s) after interaction with material (e.g., cells, particles and/or chemicals) in the jets and/or channels, and one or more detectors or detector assemblies. The plurality of spatially separated jets and/or channels may be supplied on one or more microfluidic chips or flow cells. The detectors, which may include light amplifying elements, typically detect each light signal and transduce the light signal into an electronic signal. The electronic signals, typically representing the intensity of an optical signal, generally pass from the detector(s) to an electronic data acquisition system for analysis. In certain embodiments, the light amplifying element or elements may comprise an array of phototubes, a multi-anode phototube, or a multichannel plate-based image intensifier coupled to an array of photodiode detectors.

Some objectives of the present disclosure include providing one or more of the following improvements over existing optical designs (e.g., single optical axis design, large lens pair, etc.): 1) reducing optical path length; 2) reducing complexity (e.g., design and manufacture); 3) increasing optical collection efficiency and/or performance (e.g., including reducing optical cross-talk between multiple flow measurement channels); and/or 4) isolating optical paths of light collected from a plurality of objects (e.g., flow channels).

Moreover, the systems, assemblies and methods of the present disclosure advantageously may include and provide, without limitation: 1) ensuring that other light collection paths (e.g., light extinction and/or scatter) are not obstructed; 2) retaining a high numerical aperture and/or imaging performance, and/or 3) taking jet and/or channel width, chip and/or flow cell thickness and/or working distance into account.

A number of advantageous and design approaches were investigated for the systems, assemblies and methods of the present disclosure, including, without limitation: 1) spherical lens arrays; 2) aspheric lens arrays; 3) grin (gradient index) lens arrays; 4) mirror array collection systems; 5) bare fiber and other systems including lithography (e.g., planar monolithic and stacked planar systems); and/or 6) other reflective, diffractive and/or refractive approaches.

In certain aspects of the present disclosure, the particle processing systems may utilize an aspheric lens array. Even more advantageously, according to certain exemplary embodiments, the particle processing systems may include an aspheric micro-lens array optical assembly.

Further, in certain embodiments of the present disclosure, the optical systems for particle processing systems may include one or more of the following: 1) a slight tilt to the lens system (e.g., to avoid blocking other light paths); 2) bevel to the lens array and/or to the lens elements themselves; 3) spectrally selective optical elements (e.g., optical filter, spectral dispersion elements, etc.) within the housing; 4) spatial and/or angularly selective elements; 5) isolation of optical paths, and/or 6) pinned or other high-precision locating features for assembling the components.

Embodiments include a micro-lens system, a micro-lens array, a micro-lens array for collecting and collimating light from a plurality of micro channels associated with a plurality of flow cytometers, and a multi-channel microfluidic system including such micro-lens array.

An embodiment includes a micro-lens array for collecting and collimating light from a plurality of micro channels associated with a plurality of flow cytometers. The micro-lens array includes a plurality of micro-lens system disposed along the optical paths of the plurality of micro channels of the system. Further, the micro-lens array may include a housing for mounting the plurality of micro-lens systems along the plurality of optical paths and for integrating the plurality of micro-lens systems with a fiber array. In some embodiments, the optical system is configured for simultaneously collecting fluorescent light emitted by a plurality of particles flowing in a plurality of micro channels.

The present disclosure provides a particle processing system including a particle processing region and a detection region including a micro-lens array optical assembly, wherein the particle processing region, detection region and micro-lens array optical assembly are configured and adapted to process particles. The particle processing region may be provided on microfluidic chips that are removably and interchangeably configured for optical communication with the detection region and the micro-lens systems described herein.

Embodiments provide a micro-lens optical system for collecting signals (e.g., light) from a plurality of micro channels associated with a plurality of flow cytometers, and a multi-channel microfluidic system including the optical system. Certain embodiments provide a micro-lens optical system for collimating and/or focusing signals from a plurality of micro channels associated with a plurality of flow cytometers. The present invention is described below relative to illustrative embodiments. Those skilled in the art will appreciate that the present invention may be implemented in a number of different applications and embodiments and is not specifically limited in its application to the particular embodiments depicted herein.

The present disclosure also provides for a particle processing system wherein the micro-lens array optical assembly includes an aspheric lens array or an aspheric micro-lens array optical assembly. The present disclosure provides for a particle processing system wherein the micro-lens array optical detection assembly includes one or more of the following features: a slight tilt to the lens system to avoid blocking other light paths, a bevel to the lens array and/or micro-lens system, spectrally selective optical elements or optical filters within the housing, isolation of optical paths, and/or pinned or other high-precision locating features for assembling the components.

The present disclosure is further described with respect to the following examples; however, the scope of the disclosure is not limited thereby. The following examples illustrate the systems and methods of the present disclosure of providing optical systems for particle processing (e.g., cytometry including microfluidic based sorters, drop sorters, and/or cell purification) systems and methods.

As used herein, the term particles includes, but is not limited to, cells (e.g., blood platelets, white blood cells, tumorous cells, embryonic cells, spermatozoa, etc.), synthetic beads (e.g., polystyrene), organelles, and multi-cellular organisms. Particles may include liposomes, proteoliposomes, yeast, bacteria, viruses, pollens, algae, or the like. Particles may also refer to non-biological particles. For example, particles may include metals, minerals, polymeric substances, glasses, ceramics, composites, or the like. Additionally, particles may include cells, genetic material, RNA, DNA, fragments, proteins, etc. or beads with fluorochrome conjugated antibodies.

As used herein, the term "microfluidic" refers to a system or device for handling, processing, ejecting and/or analyzing a fluid sample including at least one channel having microscale dimensions. The term "channel" as used herein refers to a pathway formed in or through a medium that allows for movement of fluids, such as liquids and gases. The term "micro channel" refers to a channel, preferably formed in a microfluidic system or device, having cross-sectional dimensions in the range between about 1.0 µm and about 2000 µm, preferably between about 25 µm and about 500 µm, and most preferably between about 50 µm and about 300 µm. One of ordinary skill in the art will be able to determine an appropriate volume and length of the channel for the desired application. The ranges above are intended to include the above-recited values as upper or lower limits. The channel may have any selected cross-sectional shape or arrangement, non-limiting examples of which include a linear or non-linear configuration, a U-shaped or D-shaped configuration, and/or a rectangular, triangular, elliptical/oval, circular, square, or trapezoidal geometry. A microfluidic device or chip may include any suitable number of channels for transporting fluids. The microfluidic chip may include a disposable cartridge with a closed channel system of capillary size.

A microfluidic particle (e.g., cell) sorting system for a microfluidic chip, in accordance some embodiments, may have a wide variety of applications as a therapeutic medical device enabling cell-based therapies, such as blood transfusion, bone marrow transplants, and/or mobilized peripheral blood implants. Embodiments of microfluidic sorting systems may be capable of selecting cells based on intrinsic characteristics as determined by interaction of light with the cells (e.g., scatter, reflection, and/or auto fluorescence) independent of protocols and necessary reagents. A microfluidic system may employ a closed, sterile, disposable cartridge including a microfluidic chip. The microfluidic system may process particles (e.g., cells) at high speeds, and deliver particles (e.g., cells) with high yield and high purity.

Example 1: Microfluidic Flow Sorter Particle Processing System

Referring now to FIG. 1, a particle processing system 200 may be configured, dimensioned and adapted for analyzing, sorting, and/or processing (e.g., purifying, measuring, isolating, detecting, monitoring and/or enriching) particles (e.g., cells, microscopic particles, etc.) or the like. For example, system 200 may be a cytometer and/or a cell purification system or the like, although the present disclosure is not limited thereto. Rather, system 200 may take a variety of forms, and it is noted that the systems and methods described may be applied to other particle processing systems.

In exemplary embodiments, system 200 is a microfluidic flow sorter particle processing system 200 (e.g., microfluidic chip based system) or the like. Exemplary microfluidic flow sorter particle processing systems and components or the like are disclosed, for example, in U.S. Pat. No. 8,529,161 (Ser. No. 13/179,084); U.S. Pat. No. 8,277,764 (Ser. No. 11/295,183); U.S. Pat. No. 8,123,044 (Ser. No. 11/800,469); U.S. Pat. No. 7,569,788 (Ser. No. 11/101,038); U.S. Pat. No. 7,492,522 (Ser. No. 11/906,621) and U.S. Pat. No. 6,808,075 (Ser. No. 10/179,488); and US Patent Publication Nos. 2012/0277902 (Ser. No. 13/342,756); 2011/0196637 (Ser. No. 13/022,525) and 2009/0116005 (Ser. No. 12/259,235); and U.S. Patent Application Ser. No. 61/647,821 (Ser. No. 13/896,213) and 61/702,114 (Ser. No. 14/029,485), the foregoing being incorporated herein by reference in their entireties.

In further exemplary embodiments, system 200 is a multi-channel or multi-jet flow sorter particle processing system (e.g., multiple capillaries or multiple fluid jet-based systems) or the like. Exemplary multi-channel or multi-jet flow sorter particle processing systems and components or the like are disclosed, for example, in US Patent Publication No. 2005/0112541 (Ser. No. 10/812,351), the entire contents of which is hereby incorporated by reference in its entirety.

FIG. 1 illustrates a system 200 suitable for implementing an illustrative embodiment of the present disclosure. System 200 includes a microfluidic assembly 220 (e.g., microfluidic chip). Microfluidic assembly 220 includes and/or is in communication with a particle inspection region and a sample fluid input region. Microfluidic assembly 220 includes a plurality of channels for conveying a substance, such as particles or cells, therethrough. In certain embodiments and as can be understood by those familiar in the art, microfluidic assembly 220 may be a combination of cuvettes, capillaries, nozzles, or jets which may combine to produce a multichannel particle processing system. The channels transport fluid and/or particles through the assembly 220 for processing, handling, and/or performing any suitable operation (e.g., on a liquid sample). Assembly 220 may include any suitable number of micro channels for transporting fluids through assembly 220. Alternatively, a lesser number of channels than particle paths is envisaged whereby, for example, multiple particle streams are injected into a single microfluidic channel.

In exemplary embodiments, an optical detector system 226 for use with microfluidic assembly 220 is provided. At least a portion of optical detector system 226 may be implemented in a particle inspection region configured for the interrogation of the particles in this region.

At least a portion of the optical detector system 226 may monitor flow through a plurality of channels simultaneously. In exemplary embodiments, system 226 can inspect individual particles for one or more particular characteristics, such as size, form, fluorescence, optical scattering, as well as other characteristics. It is noted that system 226 is not limited for use in particle or cell sorting systems and may be implemented in any suitable system having a substance, such as particles, to be monitored within one or more channels.

Figure 3:
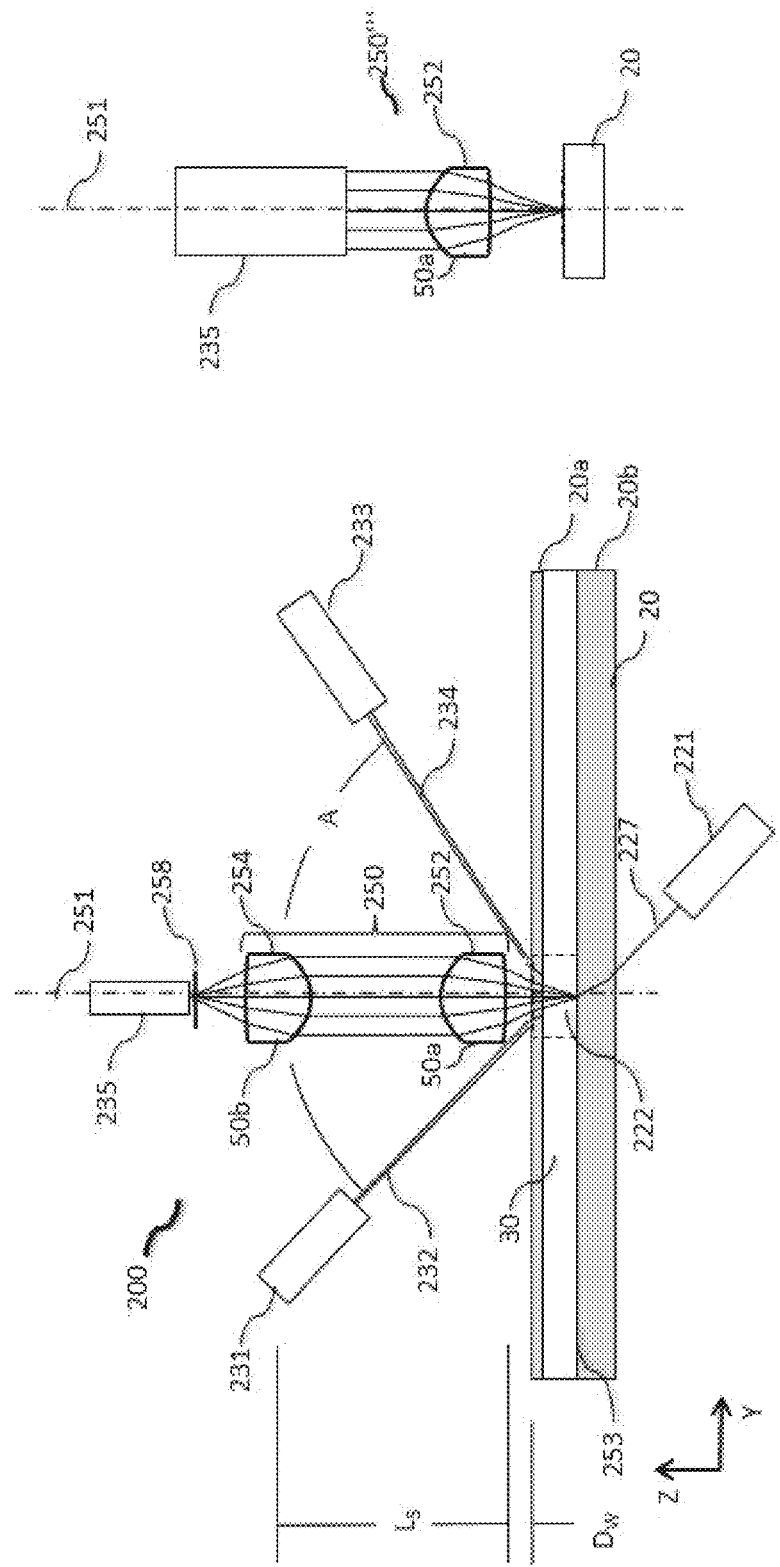
FIGS. 3A and 3B schematically illustrate exemplary particle processing systems and micro-lens systems according to the present disclosure.

System 200 also includes at least one electromagnetic radiation or light source 221 (e.g., a laser source or the like) for simultaneously or sequentially illuminating at least a portion of each of the microfluidics channels 30 (e.g., an interrogation region 222) (see also FIG. 3). The electromagnetic radiation source 221 may be coupled to and/or in communication with beam shaping optics 225 (e.g., segmented mirror/mirrors or the like) for producing and forming a beam of electromagnetic radiation (e.g., light) 227. The light source 221 may be provide as one or more monochromatic light sources, polychromatic light sources, or any combination of the aforementioned. As a non-limiting example, the light source 221 may be an optical pumped semiconductor (OPS) laser device producing about 200 mW, 2 W, or 10 W at a wavelength of 488 nm with minimal optical noise. As another non-limiting example, a diode pumped solid state (DPSS) laser may be used, which is capable of generating different wavelengths of light, such as 355 nm at 300 mW or 2 W, or 532 nm at 1 W, 2 W, 5 W, or 10 W for excitation and/or illumination. In general, the electromagnetic radiation source(s) 221 may have any suitable wavelength and one skilled in the art will recognize that any suitable light source(s) may be used.

In some embodiments, the one or more radiation beams 227 may pass through an optical mask aligned with the plurality of particle-conveying channels in the microfluidic chip assembly 220. The optical mask may take the form of an array of pinholes with each pinhole corresponding to a channel 30. The electromagnetic radiation admitted by the pinholes subsequently passes through the conveying channels themselves. The portion of electromagnetic radiation beam 227 admitted to each channel via one or more associated pinholes may intersect and/or interact with particles that are conveyed through the channel to create optical signals.

Examples of optical signals that may be produced in optical particle analysis, cytometry and/or sorting when a beam 227 intersects a particle include, without limitation, optical extinction, angle dependent optical scatter (forward and/or side scatter) and fluorescence. Optical extinction refers to the amount of electromagnetic radiation or light that a particle extinguishes, absorbs, or blocks. Angle dependent optical scatter refers to the fraction of electromagnetic radiation that is scattered or bent at each angle away from or toward the incident electromagnetic radiation beam. Fluorescent electromagnetic radiation may be electromagnetic radiation that is absorbed and/or scattered by molecules associated with a particle or cell and re-emitted at a different wavelength. In some instances, fluorescent detection may be performed using intrinsically fluorescent molecules.

In exemplary embodiments, optical detector system 226 may include one or more detector subsystems 230 to capture and observe the optical signals generated by the intersection of electromagnetic radiation beam 227 with a particle in a channel. Detector subsystems 230 may include one or more extinction detector assemblies 231 for capturing extinction signals, one or more scatter detector assemblies 233 for capturing scatter signals, and one or more fluorescence detector assemblies 235 for capturing fluorescence signals. In a preferred embodiment, detector system 226 may include at least one extinction detector assembly 231, at least one scatter detector assembly 233, and at least one fluorescence detector assembly 235. Detector assemblies 231, 233, 235 may include photomultipliers, photodiodes, cameras, or other suitable device(s). Further, detector assemblies 231, 233, 235 may include fiber optics or other waveguide-type optical transmission elements to direct the signals to the sensor elements.

According to certain embodiments, a single detector subsystem 230 may be associated with a plurality of microfluidic channels and thus, may receive signals (simultaneously, sequentially, overlapping, non-overlapping, etc.) from each of the plurality of channels. The detector assemblies 231, 233, 235 may be connected to electronics (not shown) to analyze the signals received from the detector assemblies and/or control one or more aspects of the particle sorting system 200.

Still referring to FIG. 1, each detector assembly 231, 233, 235 may be associated with optical signal collecting and transmitting elements. For example, each detector assembly 231, 233, 235 may be associated with a fiber optic array 232, 234, 236, respectively. Fiber optic arrays 232, 234, 236 may extend between the image plane (and the interrogation region 222) and the detectors 231, 233, 235 to convey signals to detector assemblies 231, 233, 235 for receiving and analyzing the signals. The fiber optic arrays 232, 234, 236 may include optical fiber coupler-splitters. Additionally, one or more of the detector subsystems 230 may include one or more lenses, filters, mirrors, and/or other optical elements to collect, shape, transmit, etc. the signal exiting the interrogation region 222 and being received by the detector assemblies 231, 233, 235. According to certain embodiments, there may be a one-to-one correspondence between an optical fiber and a micro channel 30 for any specific signal (e.g., extinction, scatter, fluorescence).

According to certain embodiments and referring to FIG. 2, microfluidic assembly 220 may be configured as a microfluidic chip 20 and may include a substrate 21 having a plurality of channels 30 (e.g., micro channels) disposed therein. The channels 30 may be configured to transport fluid and/or particles through the microfluidic chip 20 for processing, handling, and/or performing any suitable operation on a liquid sample (e.g., a particle sorting system). For example, each micro channel 30 may be a flow cytometer. The channels 30 may be arranged parallel to each other.

As best shown in FIG. 2, the microfluidic chip 20 may include an input region 24 in which a sample containing particles (e.g., cells) are input into the microfluidic chip 20. The sample may be input through a first side 28 of the microfluidic chip. Each micro channel has an interrogation region 222 associated therewith. Particles in channels 30 may be detected while flowing through the interrogation region 222. At the interrogation region 222, individual particles may be inspected or measured for a particular characteristic, such as size, form, orientation, fluorescence intensity, etc. Interrogation region 222 may be illuminated through a second side 29 of the microfluidic chip (see FIG. 2). The microfluidic chip 20 may have a plurality of channels 30 (e.g., micro channels), with the interrogation regions 222 of the plurality of channels 30 distributed across a source area 22.

The micro channels 30 may be evenly spaced in the source area 22. According to certain embodiments, a centerline-to-centerline spacing between the channels 30 may range from 0.2 mm to 5.0 mm. The centerline-to-centerline spacing between the micro channels 30 may be less than 4.0 mm, less than 3.0 mm, or even less than 1.0 mm. According to certain embodiments, the centerline-to-centerline spacing between the micro channels 30 may range from 2.5 mm to 3.0 mm. Advantageously, to minimize the footprint of the microfluidic chip 20, the centerline-to-centerline spacing between the micro channels 30 may be less than 2.0 mm, less than 1.5 mm, or even less than 1.0 mm. According to certain embodiments, the centerline-to-centerline spacing between the micro channels 30 may range from 0.7 mm to 1.2 mm.

Figure 4:
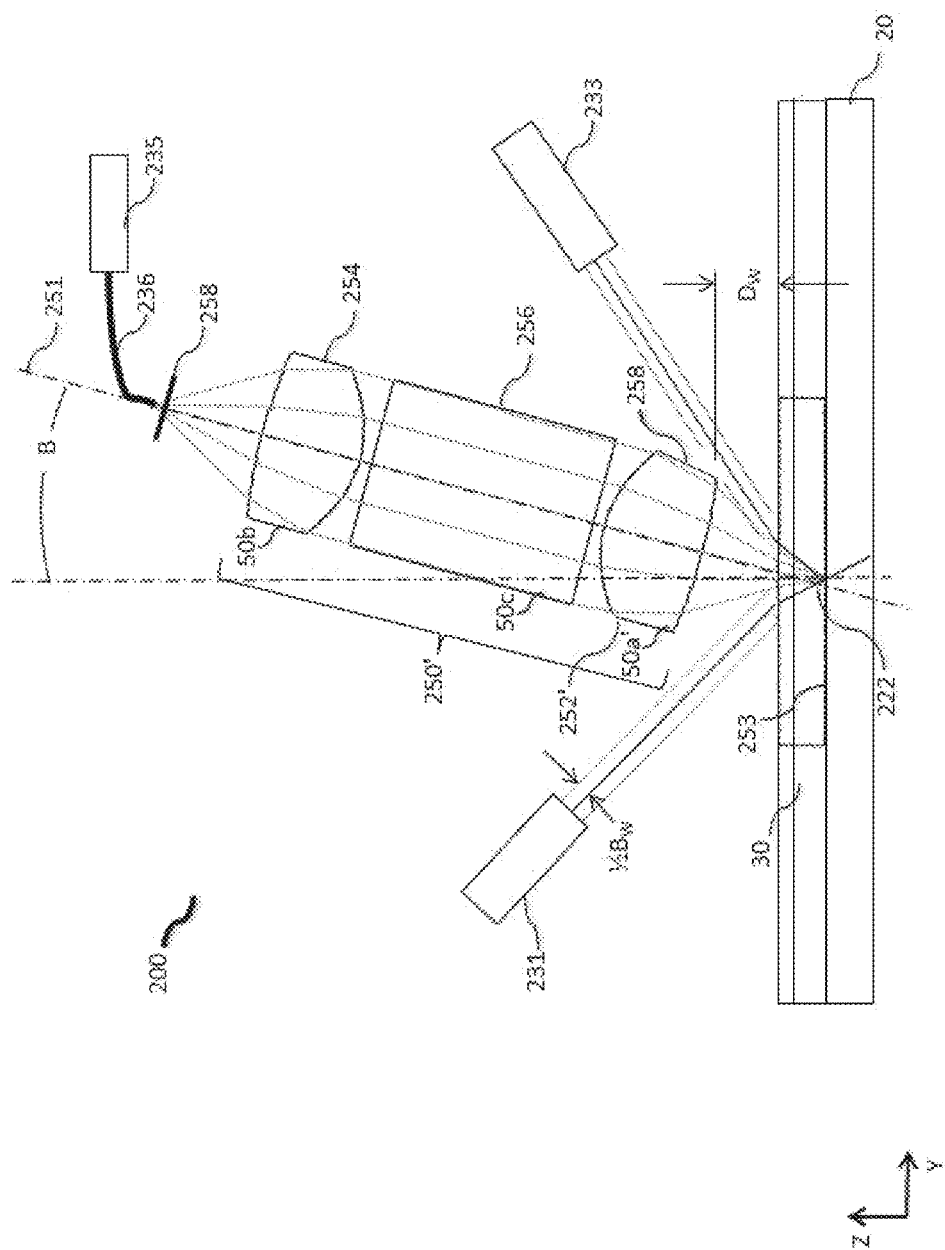
FIG. 4 schematically illustrates exemplary particle processing systems and micro-lens systems according to the present disclosure.

The microfluidic chip 20 may be formed with one or more substrate layers. As best shown in FIGS. 3A and 4, the microfluidic chip 20 may be formed with a first substrate layer 20a with the micro channel 30 (and, thus, also the interrogation region 222) formed therein. The substrate of the microfluidic layer may be glass, PDMS, PMMA, COC, or any other suitably transmissive material. The thickness of the first substrate layer 20a may range from approximately 100 μm up to approximately 1000 μm. In certain preferred embodiments, the thickness of substrate layer 20a may range from approximately 200 μm up to approximately 600 μm. For example, the thickness of substrate layer 20a may be approximately 400 μm. In other preferred embodiments, the thickness of substrate layer 20a may range from approximately 500 μm up to approximately 900 μm. By way of non-limiting examples, the thickness of substrate layer 20a may be approximately 700 μm or approximately 750 μm. In certain embodiments, the microfluidic chip 20 may be formed with only two substrate layers 20a, 20b.

Referring now to FIG. 2, microfluidic chip 20 may include twenty-four channels 30 flowing through the source area 22. One of ordinary skill in the art will appreciate that microfluidic chip 20 may include more channels or fewer channels flowing through the source area (e.g., as non-limiting examples, 2, 4, 8, 24, 36, 72, 144, or 288 channels). According to some embodiments, when microfluidic chip 20 has twenty-four micro channels 30, the source area may have an overall length extending across the plurality of channels 30 ranging from 70 mm to 80 mm.

According to certain embodiments, each of the plurality of micro channels 30 may include a sorting mechanism for directing particles flowing within the channel into various downstream channels. The sorting mechanisms may be located within one or more sorting regions 26 on the microfluidic chip 20. Sorting may be accomplished through one or more sorting mechanisms, which may include but are not limited to: mechanical displacement of the particle by deflecting a membrane with a piezoelectric actuator, pressure due to thermal actuators, optical force techniques, dielectric methods, and other suitable sort mechanisms or techniques.

The particle processing system 200 may include a receptacle or holder for removably receiving microfluidic chip 20. Further, the particle processing system 200 may include one or more stages for positioning the microfluidic chip 20 relative to the optical detection system 226. The stages may allow for movement (translation and/or rotation) of the microfluidic chip 20 and/or movement of optical components, such as a micro-lens array 260.

According to certain aspects, a detector subsystem 230 may include one or more micro-lens systems 250. A plurality of micro-lens systems 250 may be provided as a micro-lens array 260.

According to certain embodiments, and referring back to FIG. 1 and now also to FIG. 3A, the optical signal collecting elements (e.g., 232, 234, 236, 250) of detector assemblies 231, 233, 235 may be located on an opposite side of the microfluidic chip 20 (and of the interrogation region 222) from the electromagnetic radiation source assembly 221. Advantageously, these optical signal collecting elements are positioned as close as possible to the interrogation region of the microfluidic channel in order to receive the strongest signal. In certain embodiments, the optical signal collecting elements of optical extinction detector assembly 231, for example, a fiber array 232 associated with extinction detector assembly 231, may be placed directly opposite the electromagnetic radiation source 221, and may be aligned with the incident electromagnetic radiation path 227 for detecting optical extinction. The optical signal collecting elements of optical scatter detector assembly 233, for example, a fiber array 234 associated with scatter detector assembly 233, may be oriented substantially perpendicular to the path of the incident electromagnetic radiation beam 227 in the plane formed by the incident light vector and the microfluidic channel it intersects. Alternatively, a fiber array 234 associated with a scatter detection assembly 234, if any, may be oriented from 10 to 70 degrees, and more typically from 20 to 50 degrees) from the upper surface of the microfluidic chip substrate.

A fluorescence detector assembly 235 may capture optical signals from particle fluorescence emanating from interrogation region 222 of micro channel 30. In order to provide a strong fluorescence signal it is desired to capture as many fluorescent photons as possible and image them onto detector assembly 235. However, the fluorescence signal emitted from the interrogation region may be dispersed, and an optical signal collecting system able to collect more fluorescent photons than a fiber optic array may be desired. Thus, according to certain aspects, optical signal collecting elements for the fluorescence detector assembly 235 may include a micro-lens system 250 for collecting a fluorescence signal emitted from each microfluidic channel 30. A plurality of micro-lens systems 250 may be assembled into a micro-lens array 260 (see FIG. 1) for collecting the fluorescence signal emitted by a plurality of microfluidic channels 30. The micro-lens array 260 may be provided as a subassembly within a single housing. Advantageously, micro-lens array 260 provides a compact, multi-optical axis system easy to handle and align.

The example embodiments described herein disclose micro-lens systems 250 and/or micro-lens arrays 260 (refer to FIG. 1) in the context of a fluorescence detector assembly 235. In general, the micro-lens systems 250 and/or micro-lens arrays 260 may be associated with any signal that is emitted from an interrogation region of a particle processing system. Thus, the micro-lens systems 250 and/or micro-lens arrays 260 may be provided to collect fluorescence signals, side scatter signals, extinction and/or forward scatter signals, etc. and transmit those signals to the associated detector assemblies.

When a particle processing system 200 is configured to capture and analyze extinction signals, scatter signals and/or fluorescence signals emanating from a plurality of closely spaced micro channels 30, the area above the interrogation regions 222 may become very crowded with the competing optical signal collection systems. Referring to FIG. 3A, an electromagnetic radiation source 221 may be located below microfluidic chip 20 and may direct an electromagnetic radiation beam 227 into an interrogation region 222 of a micro channel 30. As shown, the incident light beam 227 may be provided at about a 45-degree angle relative to the channel 30. Above the interrogation region 222, an optical fiber 232 associated with extinction detector 231 may be oriented along the line of the exiting radiation beam 227 and an optical fiber 234 associated with scatter detector assembly 233 may be oriented at a side scatter angle to the radiation beam 227 (i.e., typically within plus/minus 45 degrees of the perpendicular to the radiation beam 227). The signal receiving ends of these optical fibers 232, 234 may be positioned within the immediate vicinity of the interrogation region 222. For example, the ends of the optical fibers 232, 234 may be positioned in contact with the substrate of the microfluidic chip 20. According to certain embodiments, wherein the elements are closely packed, the ends of the optical fibers 232, 234 may be positioned within 20 μm, 50 μm, 100 μm, 150 μm, up to 200 μm, or even up to 1 mm from the surface of the microfluidic chip 20. In a preferred embodiment, the ends of the optical fibers 232, 234 may be positioned from 20 μm to 80 μm from the surface of the microfluidic chip 20. In other embodiments, one or more of the ends of the optical fibers 232, 234 may be spaced from approximately 1 mm to approximately 25 mm from the surface of the microfluidic chip 20.

Thus, when all three signals (extinction, scatter, and fluorescence) are collected, the real estate available for the placement and orientation of a micro-lens system 250 for collecting and transmitting signals to the fluorescence detector assembly 235 is defined by a fluorescence signal sector delimited by the centerline of the extinction signal being collected on one side and the centerline of the scatter signal being collected on the other side. In some embodiments and referring to FIG. 3A, the fluorescence signal sector 237 has an angle A of less than 90 degrees. In other embodiments, the sector may encompass an angle A of approximately 90 degrees, or up to 100 degrees, up to 120 degrees, or even up to 140 degrees. Even further, in order not to block any portion of the excitation and/or scatter signals, the real estate for placing and locating a micro-lens system 250 for collecting and transmitting signals to a fluorescence detector assembly 235 is offset by the widths of the beams transmitting the excitation and scatter signals. For example, referring to FIG. 4, a half-width dimension (½$B_W$) for the extinction beam may range from approximately 100 μm to approximately 500 μm, with a typical half-width dimension ranging from approximately 250 μm to approximately 350 μm.

An exemplary micro-lens system 250 for collecting, collimating, and/or focusing light from an interrogation region 222 associated with a micro channel 30 is illustrated in FIG. 3A. The micro-lens system 250 is located between the optical fiber arrays 232, 234 of the extinction and scatter detection assemblies 231, 233. In this embodiment, central axis 251 (e.g., the optical path) of the micro-lens system 250 is oriented perpendicular to the plane of the microfluidic chip 20. The micro-lens system 250 may include a plurality of optical elements 50a, 50b disposed along an optical path 251 of the system. For clarity, a micro-lens mounting system has been omitted.

As shown, the micro-lens system 250 may include two optical elements 50a, 50b. The plurality of optical elements 50 may include a first lens 252 that collects light (i.e., electromagnetic radiation) from an interrogation region 222 at or near the object plane 253 of the micro-lens system 250. The first lens 252 is located closest to the interrogation region 222 and is positioned a working distance $D_W$ away from the top surface of the substrate 20a. The plurality of optical elements 50 may include a second lens 254 that images the light onto an image plane.

The first lens 252 may be an aspheric lens, as shown. The aspheric lens may be a plano-convex, biconvex, convex/concave, etc. The second lens 254 may also be an aspheric lens, as shown. Thus, as shown in FIG. 3A, micro-lens system 250 may include two aspheric lenses 252, 254. In other embodiments, some or all of the lenses may be aspheric. In yet further embodiments, some or all of the lenses may be spherical, aspheric or cylindrical.

In some embodiments, the micro-lens system 250 may include a symmetrical arrangement of optical elements 50. Such a symmetrical arrangement may reduce or eliminate aberrations (lateral chromatic aberration, longitudinal chromatic aberration, spherical aberration, distortion, coma, etc.). Thus, as shown in FIG. 3A, the first and second lenses 252, 254 may be identical lenses placed in mirror opposition to each other. In other embodiments, the first optical element may be different than the second optical element.

In the embodiment of FIG. 3A, the plurality of optical elements 50a, 50b includes first and second refractive lenses 252, 254. In other embodiments, diffractive and/or reflective elements (e.g., diffractive optics, reflective optics) may be used instead refractive lenses. Even further, the optical elements 50 forming a micro-lens system 250 may include spatial filters, spectral filters, beam splitters, gratings, etc.

FIG. 3A also shows the behavior of the plurality of optical elements 50 in the micro-lens system 250 using ray tracing. First optical element 50a may collect and may collimate the fluorescence signal. Second optical element 50b may focus the signal received from the first optical element 252. In general, the micro-lens system 250 need not collimate the fluorescence signal.

An air-gap may separate the first and second optical elements 50a, 50b. In general, the length of the air-gap, if any, is not critical. According to other embodiments, an optically transmissive spacer (e.g., glass, plastic, fluid) may be located between the optical elements 50.

In an exemplary micro-lens system 250, one or more of the optical elements 50 along the optical path may have a diameter D (or other cross-sectional dimension) less than 3.0 mm. According to a preferred embodiment, one or more of the optical elements 50 may have a diameter D between approximately 1.8 mm and approximately 2.7 mm. In other embodiments, one or more of the optical elements 50 may have a diameter D between approximately 0.5 mm and approximately 5.0 mm. In even other embodiments, one or more of the optical elements 50 may have a diameter D greater than approximately 5.0 mm. Larger or smaller diameter optical elements 50 may be provided. Further, the diameters or other cross-sectional dimensions of the optical elements 50 need not be the same.

According to preferred embodiments and still referring to FIG. 3A, the micro-lens system 250 may have a relatively short length $L_s$ measured as a distance between the first surface of the first optical element 50a along the optical path 251 and the last surface of the last optical element 50b. For example, the length $L_s$ may range from approximately 2.0 mm to approximately 25.0 mm. In a preferred embodiment, the length $L_s$ may range from approximately 5.0 mm to approximately 12.0 mm. As one example, the length $L_s$ may be less than 12.0 mm, less than 10.0 mm or even less than 8.0 mm. Longer or shorter micro-lens systems 250 may be provided.

In the exemplary micro-lens system 250 of FIG. 3A, the first optical element 50a disposed along the optical path may have an aspherical convex surface facing the object plane 253. In the exemplary micro-lens system 250 of FIG. 3A, the last optical element 50b may have an aspherical convex surface facing the image plane. For example, in the micro-lens system 250 of FIG. 3A, the lenses 252, 254 may each be a convex aspheric lens. As another example, the lenses 252, 254 may each be a plano aspheric lens.

In general, the optical components 50 may include refractive optics, reflective optics, Fresnel optics, diffractive optics, or any combination thereof, and lenses with other geometric profiles (e.g., plano, convex, concave, aspheric, toroidal, spherical, cylindrical, etc.).

In preferred embodiments, most or all of the transmissive optical elements 50 (e.g., lenses, filters, gratings) in the plurality of optical elements forming the micro-lens system 250 may include materials having relatively low auto-fluorescence. In some embodiments, each lens in the plurality of optical elements 50 may include a material having an auto-fluorescence within a range of about 200-times to about 2-times less than BK7 glass. Other materials, including for example, plastics, which may be high fluorescence materials, may be used.

The micro-lens system 250 may have a combination of optical properties that make it particularly well suited for applications involving the collection and/or collimation of light from a micro channel associated with a flow cytometer. For example, a micro-lens system 250 may have a relatively high numerical aperture. In some embodiments, a micro-lens system 250 may have a numerical aperture two-to-three times higher than a photolighography micro-fabricated continuous array system. As an example, a micro-lens system 250 may have a numerical aperture of between 0.40 and 0.60. In certain embodiments, the micro-lens system may have a numerical aperture of approximately 0.50. Further, a micro-lens system 250 may allow longer working distances $D_W$ with greater diameter D optical elements as compared to a micro-fabricated continuous array system, thus enabling the use of standard microfluidic chip systems.

According to some embodiments, the micro-lens system 250 may have an f-number (N) of less than about 2.0 (e.g., within a range of about 0.7 and 1.2) for light from all portions in the interrogation region. Such a low f-number optical system may be particularly useful for low light applications, such as collecting light from fluorescence, luminescence, phosphorescence, scattered light, plasmonic emission, and/or Raman emission.

A working distance $D_w$ between the object plane 253 and the first optical element (e.g., lens 252) of the micro-lens system 250 may be non-zero. A non-zero working distance prevents the micro-lens system 250 from physically contacting the microfluidic chip 218. Thus, the micro-lens system 250 is prevented from bending or otherwise deforming the chip 218 and the chip 281 is prevented from deforming the micro-lens system 250 and thus possibly changing the optical alignment.

The working distance $D_w$ between the object plane 253 and the first optical element (e.g., lens 252) of the micro-lens system 250 may be less than 25 mm. According to some embodiments, the working distance may range from approximately 0.05 mm to approximately 25 mm, from approximately 0.05 mm to approximately 20 mm, from approximately 0.05 mm to approximately 15 mm, from approximately 0.05 mm to approximately 10 mm, or even less than approximately 5 mm. If the working distance is too great, compared to the diameter of the closest optical element (i.e., the optical element collecting the signal) the signal intensity may be too low. Thus, for an optical element having a diameter of less than 3.0 mm, a working distance of less than 5.0 mm may be preferred. Similarly, a micro-lens having an f-number of approximately 1.0 may be preferred. A small working distance may be particularly useful in a flow cytometry system in which particles that emit or scatter light are separated from the optical system by at least fluid in the channel and/or a top surface of a microfluidic chip.

According to some embodiments, at least a portion of the working distance $D_W$ may consist of an air gap. Further, an optically transmissive spacer may be located between the micro-lens system 250 and the substrate forming the microfluidic chip 20. This spacer may assist in optimally positioning the micro-lens system 250 from the interrogation region 222. The spacer may also assist in maximizing the coupling efficiency of light from the interrogation region 222 to the micro-lens system 250.

The micro-lens system 250 may have approximately a one-to-one magnification. The magnification of the optical system may fall within a range of about 0.5 to about 5. According to other examples, the magnification of the optical system may range up to 10 times or even up to 100 times. In some embodiments, a variation in the magnification across the lens system may fall within a range of +/−5%.

The micro-lens system 250 may have a relatively small depth of field. In some embodiments, a depth of field of the optical system may be within a range of about +/−0.05 μm and about +/−1500 μm.

The point spread function of the micro-lens system 250 for various points across the source area may be characterized through encircled energy. For all light energy incident on an image plane from a point source located in the source area, the encircled energy of the lens system can be described as a percentage of the total energy incident on the source plane that is encircled by a circle of a specified radius around the centroid of the distribution (e.g., the percentage of light that falls within a circle). In some embodiments, the micro-lens system 250 may be configured such that at least 90% of the energy incident on the image plane emitted by a point source in the source area is encircled by a radius that ranges from approximately 50 μm to approximately 100 μm (or a diameter approximately 100 μm to approximately 200 μm). The encircled energy radius for at least 90% of the incident energy of the optical system may fall within a range of approximately 5 μm to approximately 500 μm. According to even other examples, the encircled energy radius for at least 90% of the incident energy of the optical system may range from approximately 0.5 μm to approximately 3 mm.

According to certain aspects and referring now to FIG. 4, a particle processing system 200 may include a micro-lens system 250 oriented at an angle B to the perpendicular to the plane of the microfluidic chip 20. In FIG. 4, the micro-lens system 250' is shown oriented at 15 degrees from the perpendicular. Typically, a micro-lens system 250 may be oriented at any angle up to 25 degrees, up to 30 degrees, or even up to 35 degrees from the perpendicular. In general, a micro-lens system 250 may be oriented at any angle up to 60 degrees or even up to 70 degrees from the perpendicular. Orienting the micro-lens system 250 at an angle may allow larger diameter micro-lens optical elements to be provided in the available real estate and/or may allow the micro-lens system to be moved closer to the interrogation region.

FIG. 4 illustrates that more than two optical elements 50 may be included in the micro-lens system 250'. For example, micro-lens system 250' may include optical elements 50a', 50b, 50c. Optical element 50a' may be an aspheric lens 252'; optical element 50b may also be an aspheric lens 254; and optical element 50c may be a filter 256.

In the configuration shown in FIG. 4, filter 256 is a long pass filter located in the air-gap between the two aspheric lenses 252', 254. A long pass filter may be used to filter out wavelengths of light associated with the light source 221 to increase the ratio of the fluorescence signals to the illumination light from the particles or from the fluid. Other types of filters may be included in the micro-lens system 250' (e.g., band pass, notch, line, low pass, high pass, cutoff, multiband, polarizer, holographic, spectrally dispersive, etc.).

Even other elements may be associated with one or more of the detector subsystems 230. For example, as shown in both FIG. 3A and FIG. 4, an aperture array 258 may be provided between the micro-lens system 250 and the detector assembly 235. In some embodiments, an array of apertures may be positioned after one or more optical elements to suppress unwanted light or other spurious signals that originate outside of the object plane.

Due to the tilted orientation of the micro-lens system 250' one corner of the lower surface of the first optical element 50a' is located closer to the microfluidic chip 20 than the other corner. Spacing between this corner of closest approach and the upper surface of the microfluidic chip 20 is defined as the edge working distance $D_W$. As the tilt of the micro-lens system 250' increases and as the diameter of the first optical element 50a' increases, the smaller the edge working distance $D_W$ becomes. The smaller this edge working distance $D_W$, the more the micro-lens system 250' encroaches on the space available for the transmission of the side scatter signal.

In order to maximize the intensity of the fluorescence signal collected, it is desired to maximize the diameter of the first optical element 50a and to minimize the edge working distance $D_W$. In order to also provide sufficient angular space for the side scatter signal, a distance d1 from the centerline CL of the optical element 50a' to the side 258 of the optical element 50a' closest to the microfluidic chip 20 may be less than a distance d2 from the centerline CL of the optical element 50a' to the side of the optical element 50a' farthest from the microfluidic chip 20. This may best be seen in FIG. 5A.

Figure 5:
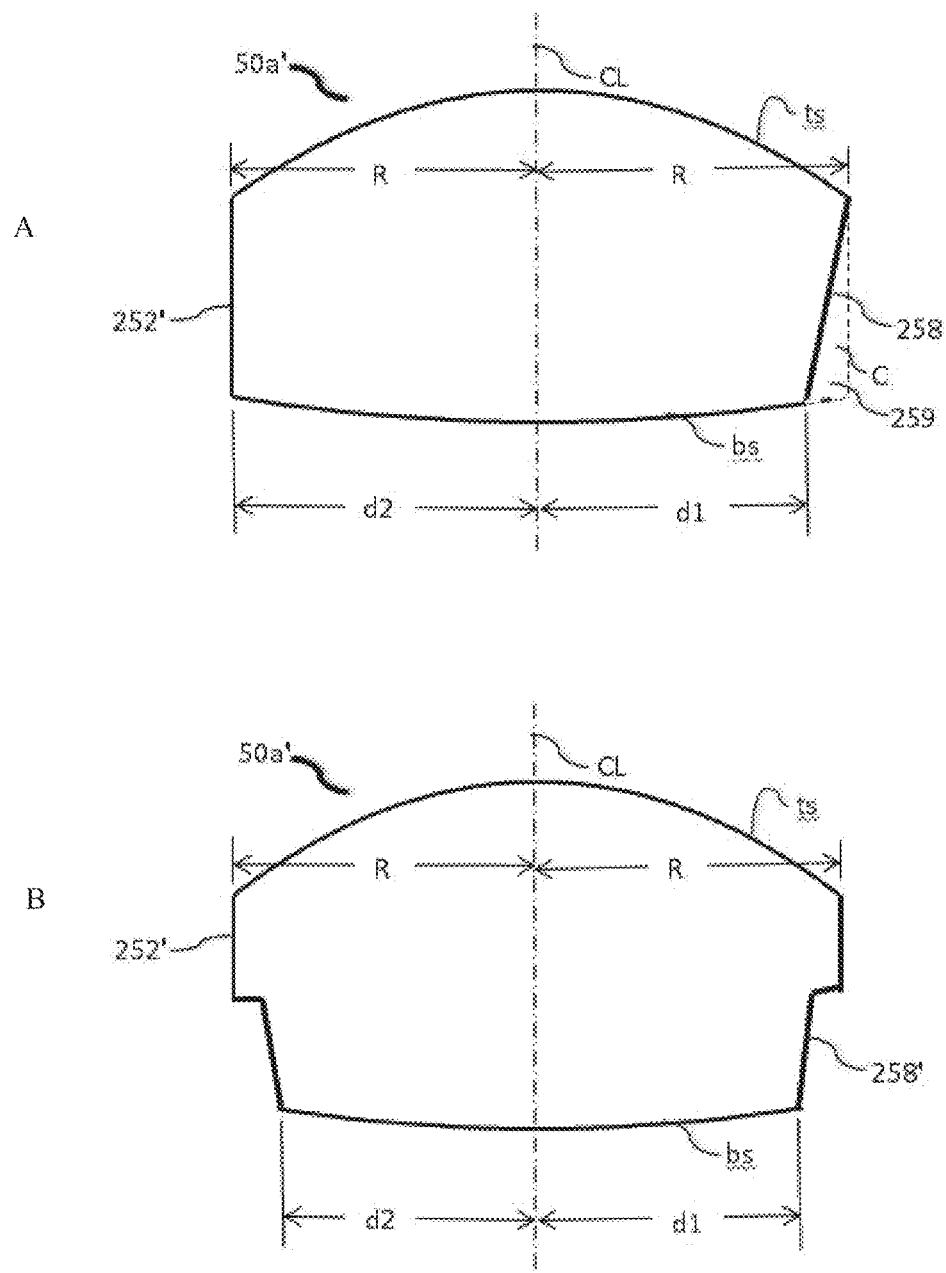
FIGS. 5A and 5B illustrate exemplary optical elements according to the present disclosure.

Further, as shown in FIG. 5A, the distance d2 may equal a radius R of the optical element 50a'. Thus, as one example, the top surface (ts) of the optical element 50a' may be provided with a fully circular cross-section having a radius R, while a bottom surface (bs) of optical element 50a' may be provided as a circular cross-section with a chord. The top surface (ts) of the optical element 50a' may have a larger perimeter than the bottom surface (bs).

Referring to FIG. 5A, in some embodiments, the side 258 of the optical element 50a' may be provided at an angle C relative to the centerline CL of the optical element. The angle C may typically range from approximately 5 degrees to approximately 45 degrees.

In some embodiments, a lowermost corner 259 of an optical element 50a' may be "removed," so that relative to a straight-sided optical component, a chamfered or beveled optical element 50a' may be provided. This "removal" of material from a lower corner 259 of the optical element 50a' may be effected by grinding down, shaving away, slicing off, dicing, truncating, or using any other method for removing material from an optical element. The material may be "removed" from a standard optical element. Optionally, this "removal" of a lower corner 259 of the optical element 50a' may be provided by molding or forming the optical element 50a' with the angled edge 258.

According to some embodiments, the portion of the optical element 50a' that is "removed" or not supplied may not significantly affect the intensity of the transmitted fluorescent signal as compared to an optical element 50 not having the portion removed. As best shown by examining the ray trace in FIG. 4, it can be seen that any portion of the fluorescent signal passing through the "removed" portion may not form part of the transmitted collimated signal. Thus, "removing" this portion 259 of the optical element 50a' may not diminish (or may not significantly diminish) the intensity of the transmitted fluorescence signal.

Even further, referring to FIG. 5B, it is understood that the optical element 50a' may have a chamfer, bevel or notch 258' provided around any portion, including a minority or a majority, of the perimeter of the bottom surface (bs). Thus, for example, such a chamfer, bevel or notch 258' may be provided around the entire perimeter of the bottom surface, such that optical element 50a' is symmetric (and d1 will equal d2). According to this embodiment, the bottom surface (bs) of the optical element 50a' will have a smaller perimeter than the top surface (ts) (and both d1 and d2 will less than R).

The micro-lens system 250' of FIG. 4 does not have a symmetric, mirror image arrangement of optical elements 50. Specifically, aspheric lens 252' is not identical to aspheric lens 254. Aspheric lens 254 is symmetrical with respect its centerline CL (which, in this embodiment, is coincident with the optical axis 251. In contrast, aspheric lens 252' is asymmetrical with respect to its centerline CL or with respect to the optical axis 251.

Figure 6:
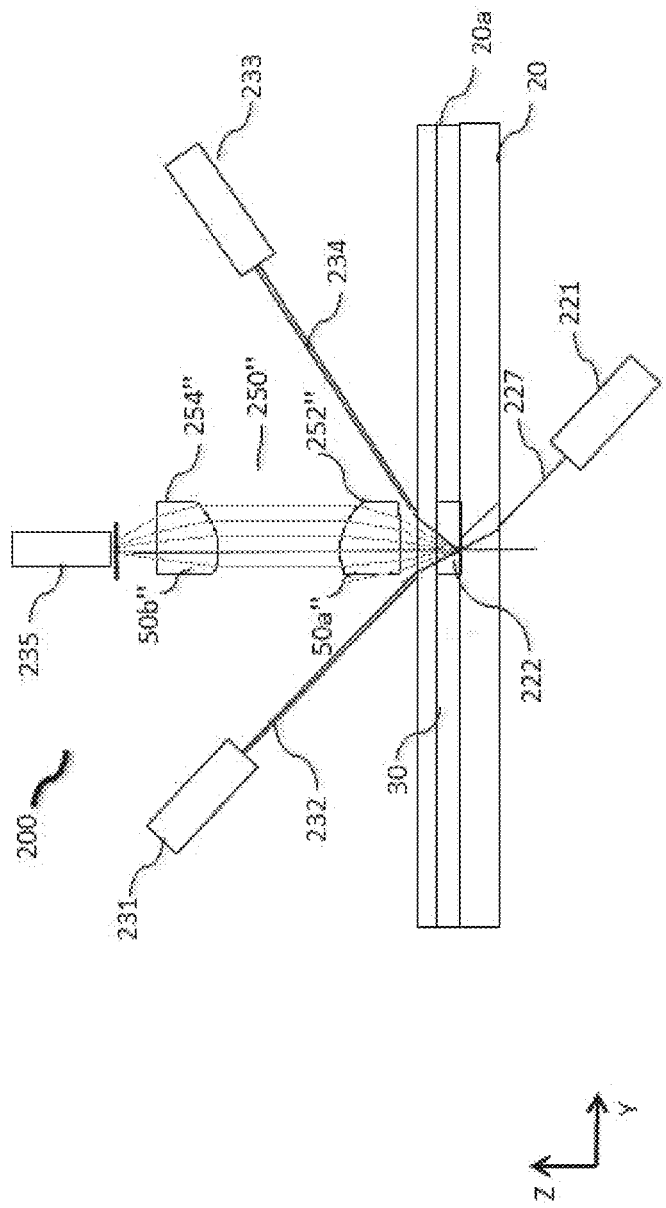
FIG. 6 schematically illustrates exemplary particle processing systems and micro-lens systems according to the present disclosure.

FIG. 6 illustrates an embodiment of a particle processing system 200 similar to the embodiment of FIG. 3, with the exception that the micro-lens system 250 of FIG. 3 has been replaced with a micro-lens system 250". Micro-lens system 250" includes a first optical element 50a" and a second identical optical element 50b". The first and second optical elements 50a", 50b" are symmetrically, mirror-image aspheric lens 252", 254" arranged along the optical path.

Figure 7:
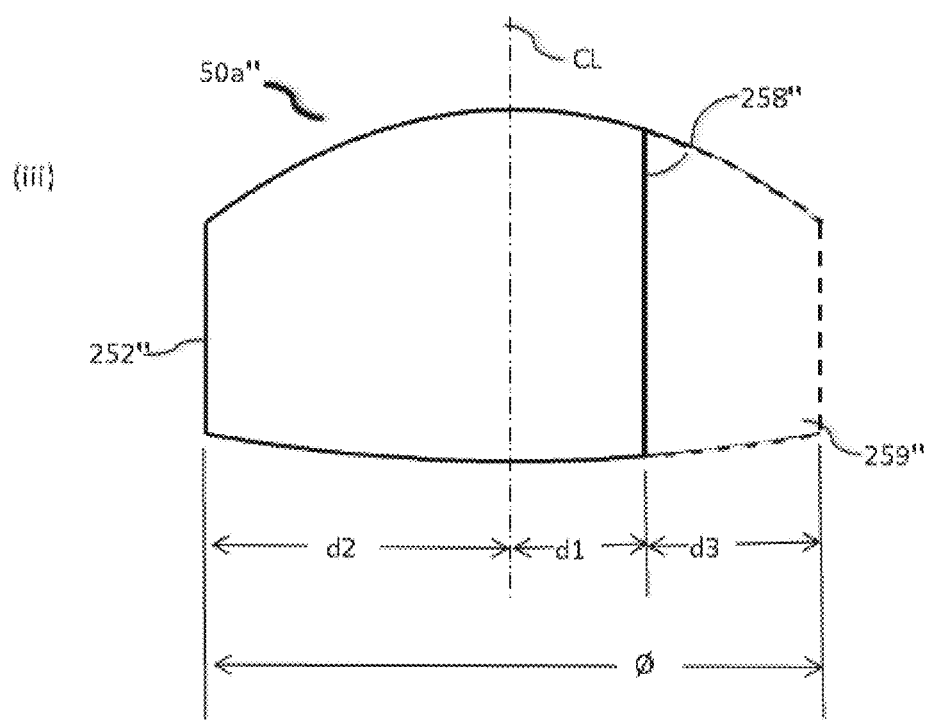
FIG. 7 illustrates exemplary optical elements according to the present disclosure.

As best shown in FIG. 7, optical element 50a" is a truncated optical element, wherein a portion 259" has been "diced off" parallel to the centerline CL of the optical element 50a. The dimension d1 is less than the dimension d2. Further, because the side 258" is parallel to the centerline CL, the perimeter of the top surface (ts) is equal to the perimeter of the bottom surface (bs). According to certain embodiments, the portion 259" "diced off" (or not supplied) may be represented by a chord (when the cross-section of the optical element 50a is considered) having a chord height or rise of d3. The chord height d3 may range from approximately 10 percent to approximately 50 percent of the diameter Ø of the non-truncated optical element 50a.

FIG. 6 illustrates the ray trace of the micro-lens system 250". The micro-lens system 250" may be oriented at any angle. Further, FIG. 6 illustrates that the truncated side of the optical component 50a" may be facing the extinction fiber assembly 232. Alternatively (not shown), the truncated side of the optical component 50a" may face the side scatter fiber assembly 234.

According to other aspects, the micro-lens system 250 may include various optical elements 50. For example, as illustrated in FIG. 8A, micro-lens system 250 may include spherical lenses 352, 354 and a filter 256 positioned therebetween. Spherical or ball lens 352 collects and collimates a signal emitted from microfluidic chip 20 and spherical lens 354 focuses the signal collimated by lens 352. According to one embodiment, lenses 352 and 354 may have a diameter of 1.1 mm, a numerical aperture of 0.5 and a working distance of 0.62 mm. According to another embodiment, lenses 352 and 354 may have a diameter of 2.5 mm, a numerical aperture of 0.5 and a focal length of 2.35 mm. In a variation, the spherical lenses 352, 354 may be provided as hemispherical lens or half-ball lenses.

As illustrated in FIG. 9A, micro-lens system 250 may include gradient index (GRIN) lenses 452, 454 and a filter 256 positioned therebetween. In general, gradient index lenses have first and second plane optical surfaces and continuously changing refractive index across the diameter of the lens. According to one embodiment, lenses 452 and 454 may have a numerical aperture of 0.46 and a focal length of 2.88 mm. According to another embodiment, lenses 452 and 454 may have a numerical aperture of 0.47 and a focal length of −3.03 mm. A GRIN lens pair may have a numerical aperture of 0.44, a focal length of −3.03 mm, an object distance of 700 µm, and an image distance of 48 µm. According to another embodiment, a GRIN lens pair may have a numerical aperture of 0.44, a focal length of −2.27 mm, an object distance of 700 µm, and an image distance of 48 µm. According to some embodiments, the numerical apertures in the embodiments may range from approximately 0.4 to approximately 0.7

As illustrated in FIG. 10A, micro-lens system 250 may include reflective optical components 552, 554 and a filter 256 positioned therebetween. According to some embodiments, the reflective optical arrays may be Schwarzschild or other reflective optical systems. The reflective optical components 552 may include a concave mirror 552b having an opening formed at the center thereof and a convex mirror 552a arranged opposite to the opening of the concave mirror. The concave mirror may have an aspherical surface. The concave mirror 552b collects the fluorescence signal emanating from the microfluidic chip 20 and reflects it to the convex mirror 552. The convex mirror 552b collimates the collected signal and sends it through the central opening formed with the concave mirror 552b. According to one embodiment, reflective components 552 and 554 may have a numerical aperture of 0.4 to 0.7 and a working distance of 0.05 mm to 25 mm.

Although certain exemplary micro-lens system 250 includes a first optical element 50a for collecting and collimating light and a second optical element 50b for focusing the light, in some embodiments, a micro-lens system 250''' may only include the first optical element 50a. Further, according to some aspects, a first set of optical elements may collect light, but not collimate the light. Thus, according to some embodiments, a single lens may be used to collect and focus the signal.

FIG. 3B illustrates that, according to some embodiments, the micro-lens system 250''' may include a single aspheric lens 252 and may include a filter 256 (not shown). FIG. 8B illustrates that, according to some embodiments, the micro-lens system 250''' may include a single spherical lens 352 and may include a filter 256 (not shown). FIG. 9B illustrates that, according to some embodiments, the micro-lens system 250''' may include a single gradient index lens 452 and a filter 256. FIG. 10B illustrates that, according to some embodiments, the micro-lens system 250''' may include a single reflective optical array 552 and may include a filter 256. According to certain other aspects, one or more additional optical systems (not shown) may be employed for focusing the collected and/or collimated signal after the signal has been transmitted by the micro-lens system 250''.

Figure 11:
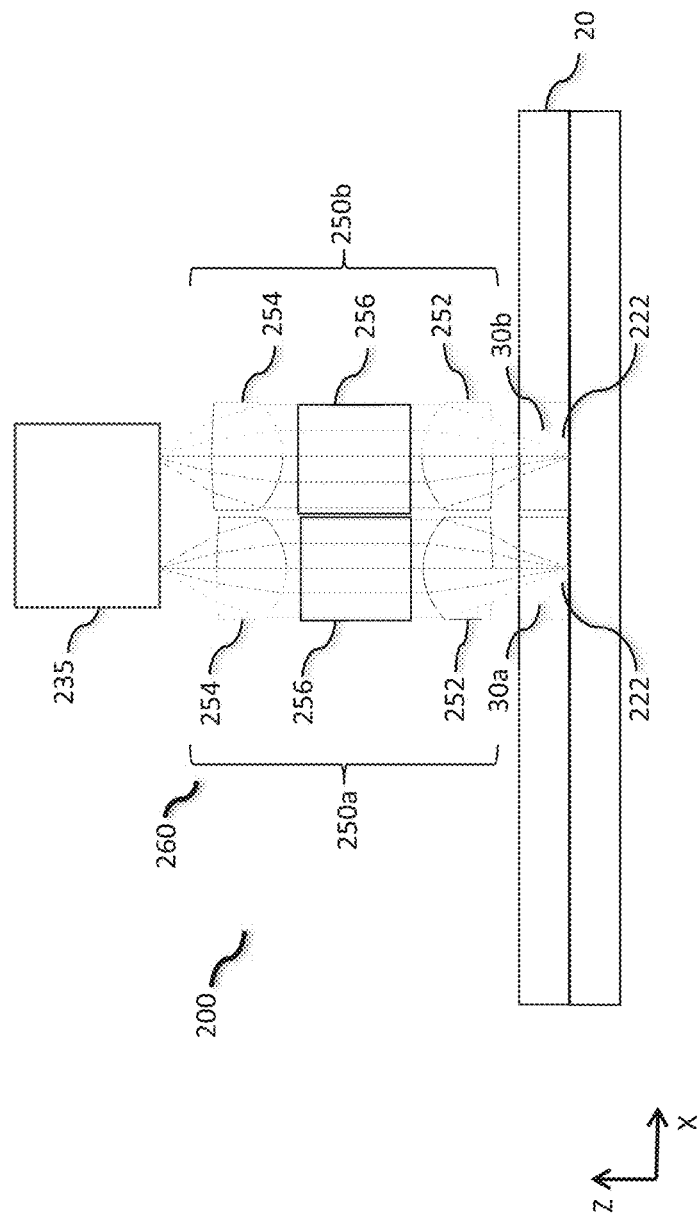
FIG. 11 schematically illustrates exemplary particle processing systems, micro-lens systems and micro-lens arrays according to the present disclosure.

FIG. 11 illustrates a micro-lens array 260 having a plurality of micro-lens systems 250a, 250b. For clarity, the mounting or housing of the micro-lens array 260 is not shown. Also, for clarity only the fluorescence detector assembly 235 is shown. Each micro-lens system 250 is associated with the interrogation regions 222 of a plurality of micro channels 30a, 30b. Any number of micro-lens systems 250 and any number of micro channels 30 may be provided. The plurality of micro-lens systems 250 may transmit signals to a single fluorescence detector assembly 235 (directly or via multiplexing). Alternatively, each micro-lens system 250 may transmit a signal to a dedicated detector assembly 235 (not shown).

As shown in FIG. 11, the micro-lens system 250a may include a pair of identical aspheric lenses 252, 254 with a filter, such as a long pass filter 256, positioned along the optical path in the air-gap between the aspheric lenses 252, 254. As shown, micro-lens system 250b may be identical to micro-lens system 250a. Alternatively (not shown), the micro-lens array 260 may include micro-lens systems 250 that are not identical. Any of the micro-lens systems 250 described herein may be included in the micro-lens array 260.

Figure 12:
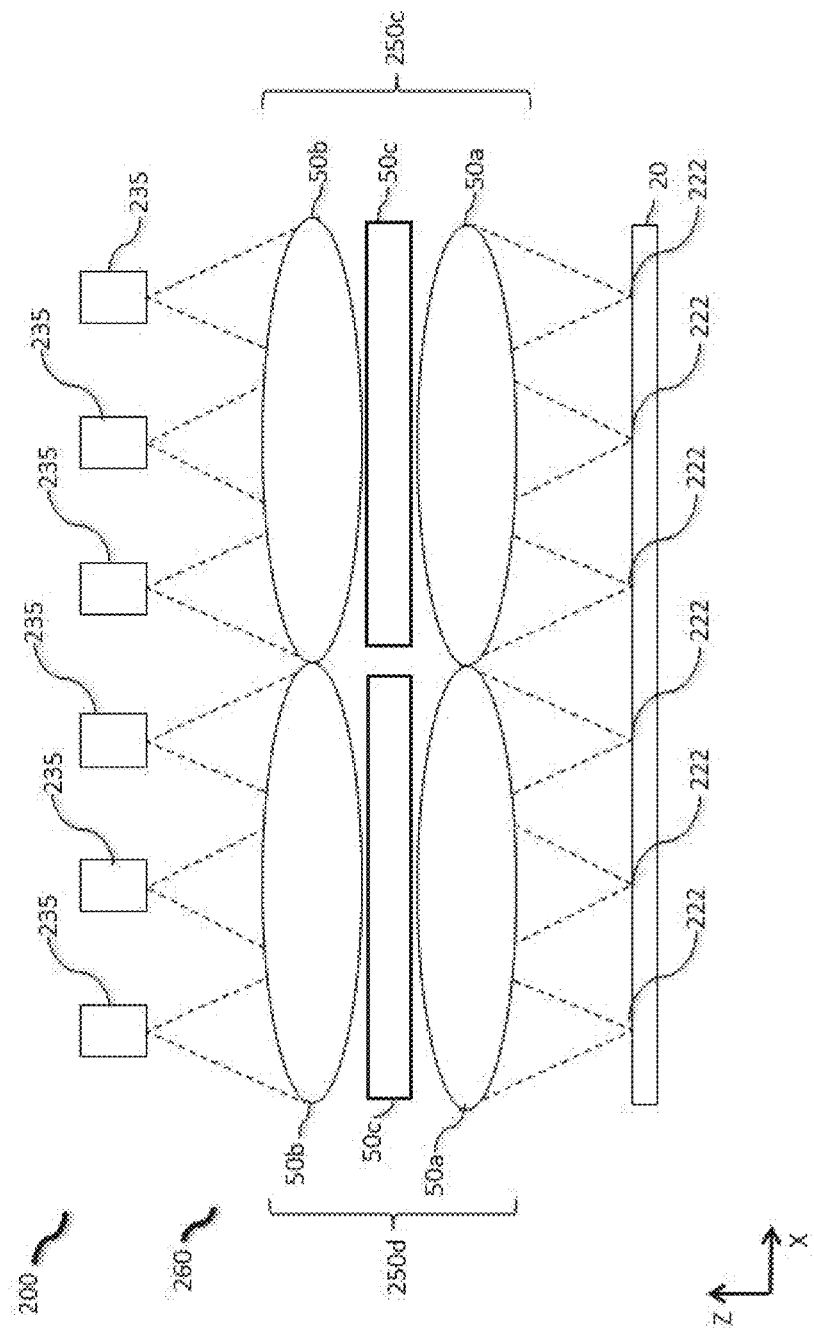
FIG. 12 schematically illustrates exemplary particle processing systems, micro-lens systems and micro-lens arrays according to the present disclosure.

FIG. 12 schematically illustrates a micro-lens array 260 wherein one or more micro-lens systems 250c, 250d may be associated with more than one micro channel 30 (and thus, with more than one interrogation region 222). For example, each micro-lens system 250c, 250d may include optical elements 50a, 50b, 50c, etc. Optical elements 50a and 50b may be aspheric lenses, wherein each lens may receive signals from a plurality of interrogation regions. Optical elements 50c may be filters. For example, the optical elements 50a, 50b may have a diameter less than 3.0 mm and the micro channels may have a centerline-to-centerline spacing of 0.9 mm, so that each micro-lens system 250 may receive signals from three microchannels. In one embodiment, a three-channel optical element may be an aspheric lens having a diameter of 2.7 mm, an approximate numerical aperture of 0.5 and a focal length of 2.14 mm. In another embodiment (not shown), a six-channel optical element may include an aspheric lens having a diameter of 5.0 mm, an approximate numerical aperture of 0.5 and a focal length of 5.14 mm. Thus, a single micro-lens system 250 may collect signals from a plurality of micro channels 30.

Figure 13:
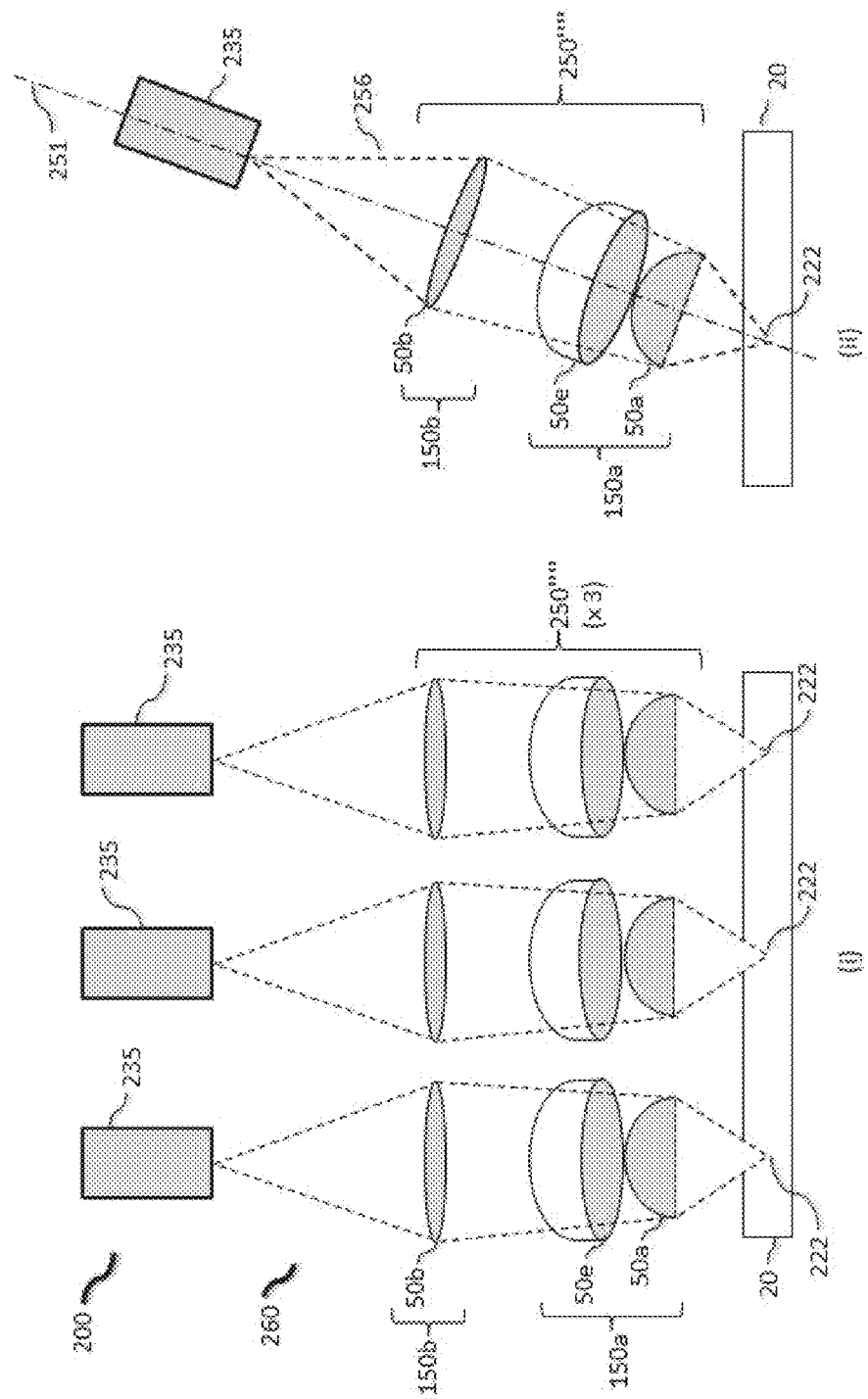
FIG. 13 schematically illustrates exemplary particle processing systems, micro-lens systems and micro-lens arrays according to the present disclosure.

FIG. 13 schematically illustrates another aspect of a micro-lens array 260. One or more of the micro-lens systems 250'''' may include a first set of optical elements 150a and/or a second set of optical elements 150b. Each set of optical elements 150 may include more than a single lens or other optical element 50. In the particular embodiment of FIG. 13, the first set of optical elements 150a includes optical elements 50a and 50e and the second set of optical elements 150b includes optical element 50b. Optical element 50a may be a plano convex lens; optical element 50e may be a positive achromatic; and optical element 50b may be a biconvex lens. In general, optical elements 50 need not be any particular micro-lens.

The first set of optical elements 150a may collect the fluorescence signal; the second set of optical elements 150b may focus the signal collected by the first set of optical elements 150a. As illustrated, there may be provided a different number of elements in the first set of optical elements from the second set of optical elements. Optionally, the first and second sets of optical elements 150 may include the same number of optical elements. Further, the first and second sets of optical elements 150 may be provided with identical optical components and, even further, the first and second sets of optical elements 150 may be symmetrically arranged as mirror images. FIG. 13(*i*) illustrates a micro-lens array 260 which has a plurality of micro-lens systems 250"". FIG. 13(*ii*) illustrates a micro-lens system 250"" orientated at an angle to the chip 20.

Figure 14:
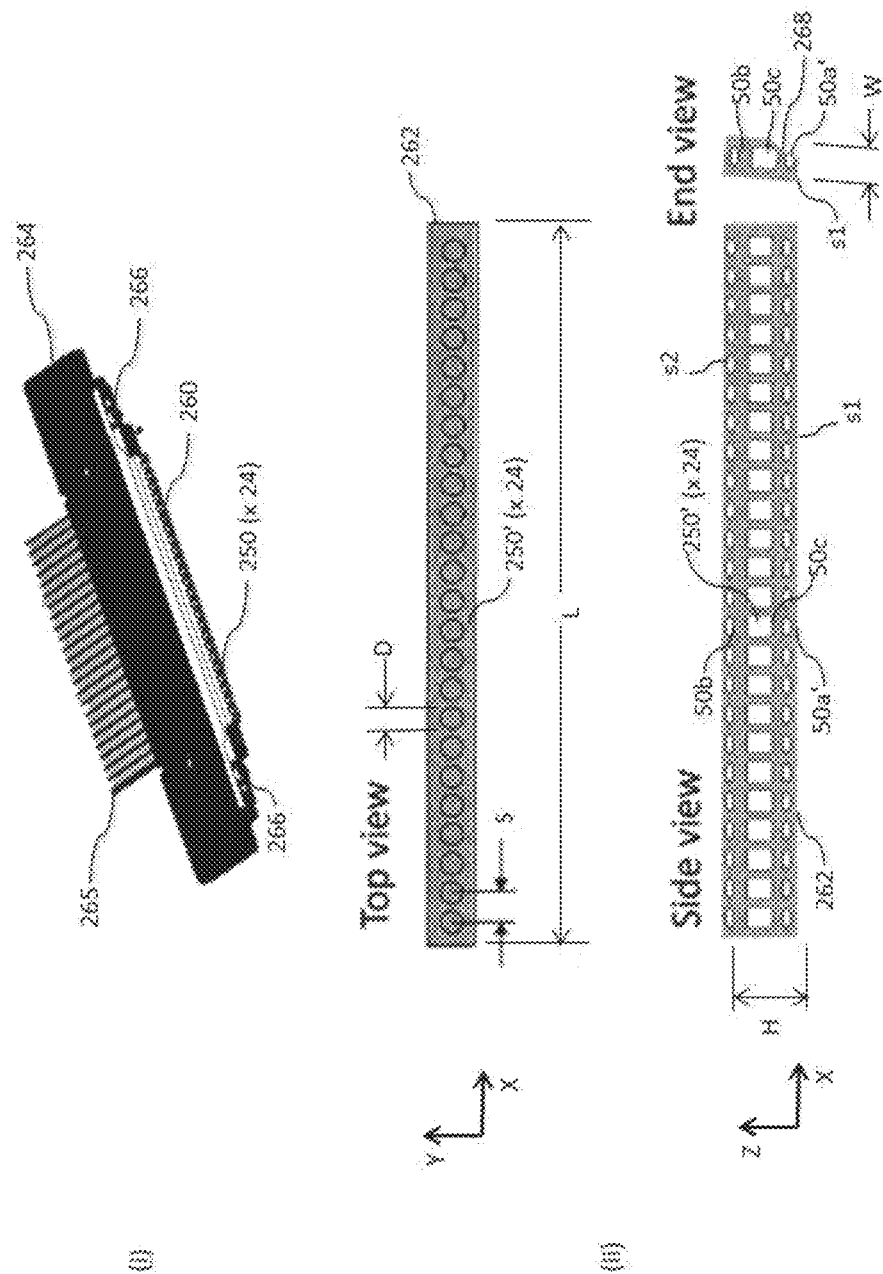
FIG. 14 illustrates a housing assembly for a micro-lens array (i) and an exemplary micro-lens array (ii) according to the present disclosure.

FIG. 14(*i*) illustrates a micro-lens array 260 having a plurality of micro-lens system 250 arranged in a linear array of twenty-four micro-lens systems 250. Any of the above-described micro-lens systems may be provided in the micro-lens array 260. As shown in FIG. 14(*i*), a housing 264 for the micro-lens array 260 may include an optical fiber to micro-lens array interface block 265. Thus, in some embodiments, micro-lens array 260 may include a plurality of optical fibers for receiving a signal from the micro-lens systems 250 and transmitting the signal to the one or more detectors. Each optical fiber may receive a signal from one microfluidic channel. Further, the housing 264 for the micro-lens array 260 may include means 266 to mount or couple the micro-lens array 260 to the remainder of the particle processing system 200.

The housing 264 may be configured to maintain the alignment and spacing of the micro-lens systems 250 relative to each other and relative to other components of the particle processing system 200. For example, the housing system 264 may include components for adjusting relative positions between the interrogation regions 220/micro channels 30 of the microfluidic chip 20 and/or between other components of a particle processing system 200. The housing 264 may provide slotted holds or other adjusting mechanisms to allow for adjustment of relative linear positions and/or relative orientations between the micro-lens systems 250 and the interrogation regions 222. The housing 264 for the micro-lens array 260 may also include spacers or stand-offs for precisely locating the micro-lens array 260 with respect to a microfluidic chip 20.

Referring to FIG. 14(*ii*), the micro-lens array 260 may include a plurality of micro-lens systems 250'. Each micro-lens system 250' may be identically provided with three optical elements 50*a*', 50*b*, 50*c*. The optical elements may include: first and second aspheric lenses and a filter. Each micro-lens system 250' is configured to be associated with an individual interrogation region 222 of a micro channel 30. For this particular embodiment, the center-to-center spacing S of the micro-lens systems 250' may be approximately 3 mm. The micro-lens array 260 may have an overall length L of approximately 75 mm, an overall width W of approximately 5 mm, and an overall height H of approximately 8 mm.

According to certain aspects, the array 260 may be assembled by encapsulating the plurality of micro-lens systems 250' in a polymeric substrate 262. As non-limiting examples, the polymeric substrate may be PDMS or other polymeric materials. A fluorescence signal from an interrogation region may enter a first surface (s1) of the substrate, may be collected, may be collimated, may be filtered, and may be focused by the micro-lens system 250' and then may exit through a second surface (s2) of the substrate.

Referring to the end view, each micro-lens system 250' may be oriented at an angle to the first surface (s1) of the substrate. For example, the micro-lens system 250' may be oriented at an angle of 15 degrees from a perpendicular to the first surface (s1) of the substrate. When the first surface (s1) of the substrate 262 is positioned relative to the microfluidic chip 20 in the source region 22, each micro-lens system 250 may be automatically aligned at a 15 degree angle from the perpendicular to the individual interrogation regions.

Further, the micro-lens array 260 may be configured to allow passage and/or reduce the blocking of an extinction signal or a scatter signal from the interrogation regions 222. For example, substrate 262 may include a chamfered region 268 to allow micro-lens the micro-lens system 250 to be placed even closer to the interrogation regions 222 without blocking some or all of the side scatter signal. This chamfer 268 may extend along the entire length of the array 260. Advantageously, this chamfer 268 of the substrate 262 may coincide with the chamfer 258 of the optical element 50*a*'.

According to other aspects, the array 260 may be assembled by providing one or more mounting blocks having through holes configured for receiving the individual optical elements 50 (or subassemblies of the individual components). Thus, for example, a micro-lens array 260 may include a first mounting portion have a first through hole configured to accommodate a first optical element 50 and a second mounting portion have a second through hole configured to accommodate a second optical element 50. For example, the through holes may be provided with stepped regions (i.e., shoulders) for seating the optical elements 50. Spacers may be provided to properly maintain the optical elements 50 within the mounting portions. The through holes may also be configured to accommodate more than one optical component, for example, by including shoulders of different diameters for seating optical elements having different diameters. Each mounting portion may maintain the alignment and spacing of the optical elements 50 in the assembly relative to each other. The first and second mounting portions may be assembled together with the first and second through holes aligned with one another, thereby forming the micro-lens array 260. High-precision locating features (e.g., pins, grooves, etc.) may be used to precision align the first and second mounting portions.

Within the micro-lens array 260, the individual optical paths for the micro-lens systems are completely isolated from one another. Thus, optical crosstalk is prohibited between adjacent micro-lens systems.

Thus, it has been disclosed that an optical signal collection subsystem for a detector assembly may include a micro-lens array 260. According to certain aspects the present disclosure provides for a particle processing system wherein a micro-lens array optical assembly may include an aspheric lens system or an aspheric micro-lens array optical assembly. The present disclosure provides for a particle processing system wherein the micro-lens array optical assembly may include one or more of the following features: a slight tilt to the lens system to avoid blocking other light paths, a finely ground bevel to the lens array, spectrally selective optical elements or optical filters within the housing, isolation of optical paths, and/or pinned high-resolution locating features.

The micro-lens array 260 may have a combination of properties that make it particularly well suited for applications involving the collection and/or collimation of light from a plurality of micro channels associated with a flow cytometer. For example, a plurality of micro-lens systems 250 may be provided, each having a relatively high numerical aperture. Additionally, a micro-lens array 260 with its discrete optical elements optically isolated within a housing may reduce optical crosstalk as opposed to a continuous micro-fabricated lens array. The micro-lens array 260 may simplify integration with the remainder of the detector assembly and alignment with the microfluidic chip. Even further, the compact assembly of the plurality of micro-lens systems 250 may allow for a smaller overall particle processing system 200.

Figure 15:
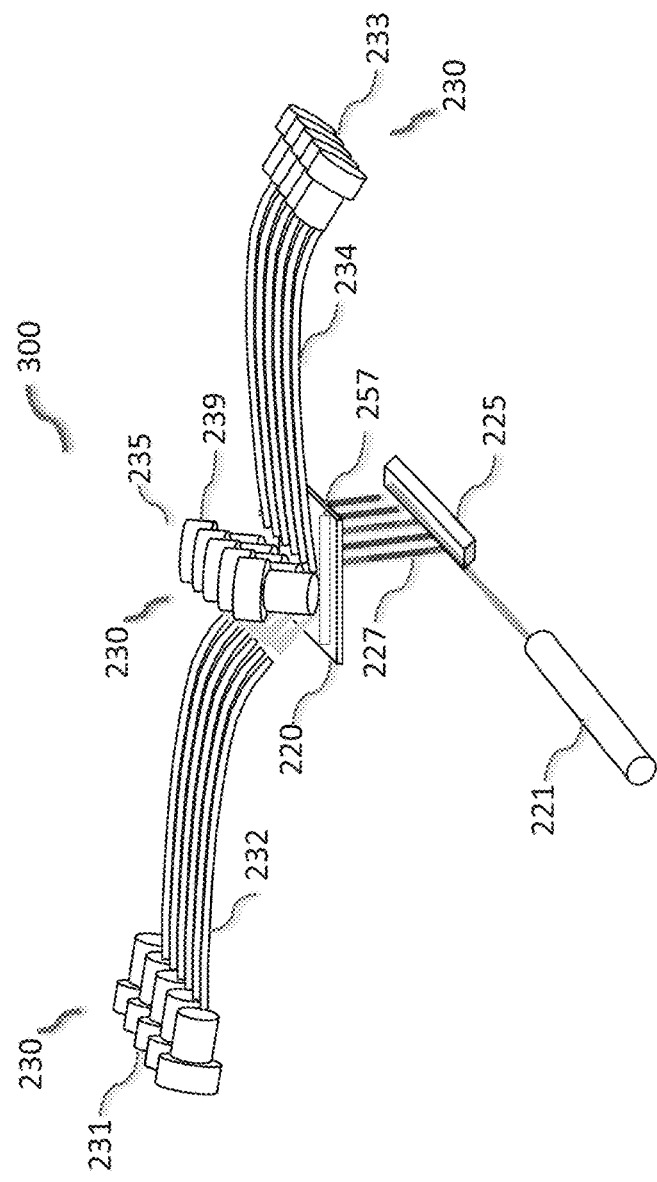
FIG. 15 schematically illustrates exemplary particle processing systems according to the present disclosure.
Figure 16:
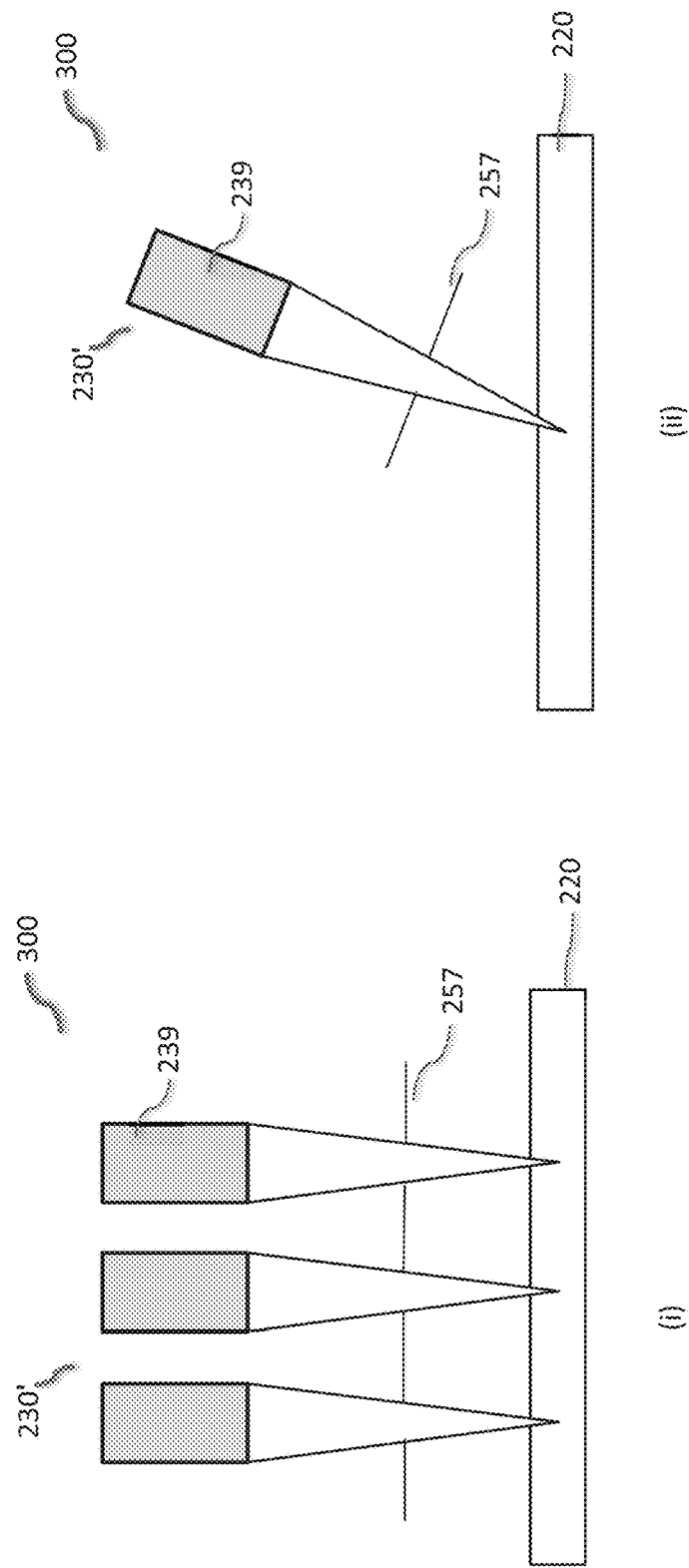
FIG. 16 schematically illustrates a (i) front view of the detector array and (ii) a side view of the detector array of FIG. 15.

According to another aspect and referring to FIGS. 15 and 16, a particle processing system 300 may include a microfluidic assembly 220, a spatial filter array 257, and a detector array 230'. Light from the interrogation region 222 of the particle processing system 300 may be selectively filtered by a spatial filter array 257 located in between the detector array 230' and the microfluidic assembly 220. The optical signal for each interrogation region 222 may then by detected by each detector element 239 in the detector array 230'. The light collection numerical aperture of each detection element 239 in the system is determined by the dimensions of the detector and the working distance of the detector from the interrogation region 222 of the microfluidic system 220. The field of view and the numerical of the detector may be determine by the dimensions of the spatial filter 257 and the distance of the spatial filter 257 from the interrogation region 222 of the microfluidic system 220 and the detector elements 239. Multiple spatial filters may be combined to match the detector array's collection angle and field of view relative to the interrogation region 222 of the microfluidic chip 220.

Although the systems, assemblies and methods of the present disclosure have been described with reference to exemplary embodiments thereof, the present disclosure is not limited to such exemplary embodiments and/or implementations. Rather, the systems, assemblies and methods of the present disclosure are susceptible to many implementations and applications, as will be readily apparent to persons skilled in the art from the disclosure hereof. The present disclosure expressly encompasses such modifications, enhancements and/or variations of the disclosed embodiments. Since many changes could be made in the above construction and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

What is claimed is:

1. A particle processing system comprising:
   a detection region including a micro-lens array; and
   a particle processing region configured to be removably and optically coupled to the detection region, wherein the particle processing region includes at least one microfluidic channel;
   wherein the micro-lens array includes at least one micro-lens system having a plurality of free-space optical elements disposed along a central axis, the micro-lens system positioned relative to the at least one microfluidic channel so as to collect light from an angle of less than 180 degrees from the at least one microfluidic channel, and
   wherein at least one optical element collects and collimates a fluorescence signal.

2. The particle processing system of claim 1, further comprising:
   a microfluidic chip having a plurality of particle interrogation regions;
   a plurality of detector assemblies configured to receive a fluorescence signal emitted from one or more of the plurality of particle interrogation regions and at least one of an extinction signal or a scatter signal emitted from one or more of the plurality of particle interrogation regions; and
   a micro-lens array including a plurality of micro-lens systems.

3. The particle processing system of claim 2, further comprising:
   a receptacle for removably receiving the microfluidic chip, wherein the microfluidic chip has a plurality of microfluidic channels; and
   one or more light sources for illuminating the plurality of particle interrogation regions.

4. The particle processing system of claim 2, wherein the micro-lens array is configured to collect fluorescence signals from the plurality of particle interrogation regions, and wherein the micro-lens array has a working distance to the microfluidic chip ranging from approximately 0.05 mm to approximately 25 mm.

5. The particle processing system of claim 4, wherein the working distance includes an air gap.

6. The particle processing system of claim 1, wherein the at least one micro-lens system includes a plurality of optical elements, wherein the microfluidic chip has a plurality of microfluidic channels, and wherein a cross-section dimension of at least one of the optical elements is approximately equal to one of the width of a microfluidic channel or the center-to-center spacing of the microfluidic channels.

7. The particle processing system of claim 1, wherein the at least one micro-lens system includes at least two aspheric lenses.

8. The particle processing system of claim 1, wherein the at least one micro-lens system has an f-number of less than approximately 2.0.

9. The particle processing system of claim 1, wherein the at least one micro-lens system includes at least one optical element that has a flat region formed on a side surface.

10. The particle processing system of claim 1, wherein the at least one micro-lens system includes at least one optical element that is asymmetric with respect to the optical axis of the optical element.

11. The particle processing system of claim 1, wherein the at least one micro-lens system includes at least one optical element that has a flat region formed on a side surface, and wherein the flat region is angled relative to the optical centerline of the optical element.

12. The particle processing system of claim 1, wherein the at least one micro-lens system includes at least one optical element that has a first surface facing the particle interrogation region, the first surface having an asymmetric cross-section.

13. The particle processing system of claim 1, wherein the at least one micro-lens system includes at least one optical element that has a diameter less than 2.0 mm.

14. The particle processing system of claim 1, wherein the central axis of the at least one micro-lens system is oriented at an angle from the perpendicular to a micro channel provided in a microfluidic chip, wherein optionally the angle ranges from approximately 5 to approximately 70 degrees.

15. The particle processing system of claim 1, wherein the optical elements of the at least one micro-lens system include two aspheric lenses and a spectral filter.

16. The particle processing system of claim 1, wherein the optical elements of the at least one micro-lens system include a gradient index lens and a spectral filter.

17. The particle processing system of claim 1, wherein the optical elements of the at least one micro-lens system include two gradient index lenses.

18. The particle processing system of claim 1, wherein the optical elements of the at least one micro-lens system include a reflective mirror array.

19. The particle processing system of claim 1, wherein the optical elements of the at least one micro-lens system include two reflective mirror arrays.

20. The particle processing system of claim 1, wherein the optical elements of the at least one micro-lens system include a spherical lens.

21. The particle processing system of claim 1, wherein the at least one micro-lens array includes a first mounting portion have a first through hole configured to accommodate a first lens for collecting and collimating a fluorescence signal and second mounting portion have a second through hole configured to accommodate a second lens for collecting and focusing the collimated fluorescence signal, and wherein the first and second mounting portions are assembled with the first and second through holes aligned with one another.

22. The particle processing system of claim 21, wherein at least one of the first through hole or the second through hole is configured to accommodate a filter.

23. The particle processing system of claim 1, wherein the at least one micro-lens system includes at least one optical element that has a diameter less than 3.0 mm.

24. A particle processing system comprising:
a detection region including a micro-lens array; and
a particle processing region configured to be removably and optically coupled to the detection region, wherein the particle processing region includes at least one microfluidic channel;
wherein the micro-lens array includes at least one micro-lens system having an asymmetric, non-mirror image arrangement of optical elements, the micro-lens system associated with and in optical communication with the at least one microfluidic channel,
wherein at least one optical element collects and collimates a fluorescence signal.

25. The particle processing system of claim 24, wherein the at least one micro-lens system having the asymmetric, non-mirror image arrangement of optical elements includes a first aspheric lens that is symmetrical with respect to its centerline and a second aspheric lens that is asymmetrical with respect to its centerline or with respect to the optical axis.

26. The particle processing system of claim 25, wherein the second aspheric lens is chamfered or beveled.

* * * * *